(12) United States Patent
Fukushi et al.

(10) Patent No.: US 10,086,148 B2
(45) Date of Patent: Oct. 2, 2018

(54) ASSEMBLY FOR SYRINGE, PREFILLED SYRINGE, SEAL CAP FOR BARREL AND PACKAGE FOR ASSEMBLY FOR SYRINGE

(71) Applicants: TERUMO KABUSHIKI KAISHA, Tokyo (JP); MCPP Innovation LLC, Tokyo (JP)

(72) Inventors: Keiko Fukushi, Hadano (JP); Yoshihiko Abe, Odawara (JP); Kanae Karube, Yokkaichi (JP)

(73) Assignees: TERUMO KABUSHIKI KAISHA, Tokyo (JP); MCPP INNOVATION LLC, Tokyo (JP)

( * ) Notice: Subject to any disclaimer, the term of this patent is extended or adjusted under 35 U.S.C. 154(b) by 0 days.

(21) Appl. No.: 15/898,904

(22) Filed: Feb. 19, 2018

(65) Prior Publication Data

US 2018/0169347 A1 Jun. 21, 2018

Related U.S. Application Data

(63) Continuation of application No. PCT/JP2016/074275, filed on Aug. 19, 2016.

(30) Foreign Application Priority Data

Aug. 20, 2015 (JP) ................. 2015-163245

(51) Int. Cl.
*A61M 5/32* (2006.01)
*A61J 1/14* (2006.01)
*A61M 5/31* (2006.01)

(52) U.S. Cl.
CPC .......... *A61M 5/3202* (2013.01); *A61J 1/1412* (2013.01); *A61M 2005/312* (2013.01); *A61M 2005/3109* (2013.01)

(58) Field of Classification Search
CPC ................ A61J 1/1412; A61M 5/3202; A61M 2005/3109; A61M 2005/312
See application file for complete search history.

(56) References Cited

U.S. PATENT DOCUMENTS 6,719,732 B2   4/2004   Courteix
8,939,941 B2   1/2015   Thibault et al.
(Continued)

FOREIGN PATENT DOCUMENTS

JP   2005-319118 A   11/2005
JP   2007-501062 A    1/2007
(Continued)

OTHER PUBLICATIONS

International Search Report issued in International Patent Application No. PCT/JP2016/074275 dated Nov. 8, 2016.
(Continued)

*Primary Examiner* — Michael C Miggins
(74) *Attorney, Agent, or Firm* — Foley & Lardner LLP

(57) ABSTRACT

An assembly of the present invention for a syringe is composed of a barrel, made of cyclic polyolefin, which has a barrel body having a distal end part and a piercing needle which has a piercing needle tip at its distal end and is fixed to a piercing needle fixing portion of the barrel and a seal cap mounted on the barrel. The seal cap is formed of a thermoplastic elastomer composition containing as its main component a mixture of a styrene-based thermoplastic elastomer and a softener, for hydrocarbon-based rubber, which has a kinematic viscosity of 1 to 5,000 $mm^2 s^{-1}$ at 100 degrees C. and a naphthenic carbon ratio (% CN) of not more than 20% when said naphthenic carbon ratio is measured by ring analysis.

18 Claims, 16 Drawing Sheets

(56) References Cited

U.S. PATENT DOCUMENTS

2004/0111066 A1  6/2004  Prais et al.
2016/0008553 A1  1/2016  Fournier et al.

FOREIGN PATENT DOCUMENTS

| JP | 2010-534546 A | 11/2010 |
| WO | WO-2009/016428 A1 | 2/2009 |
| WO | WO-2014/131987 A1 | 9/2014 |

OTHER PUBLICATIONS

International Preliminary Report on Patentability dated Mar. 1, 2018 in corresponding application PCT/JP2016/074275.

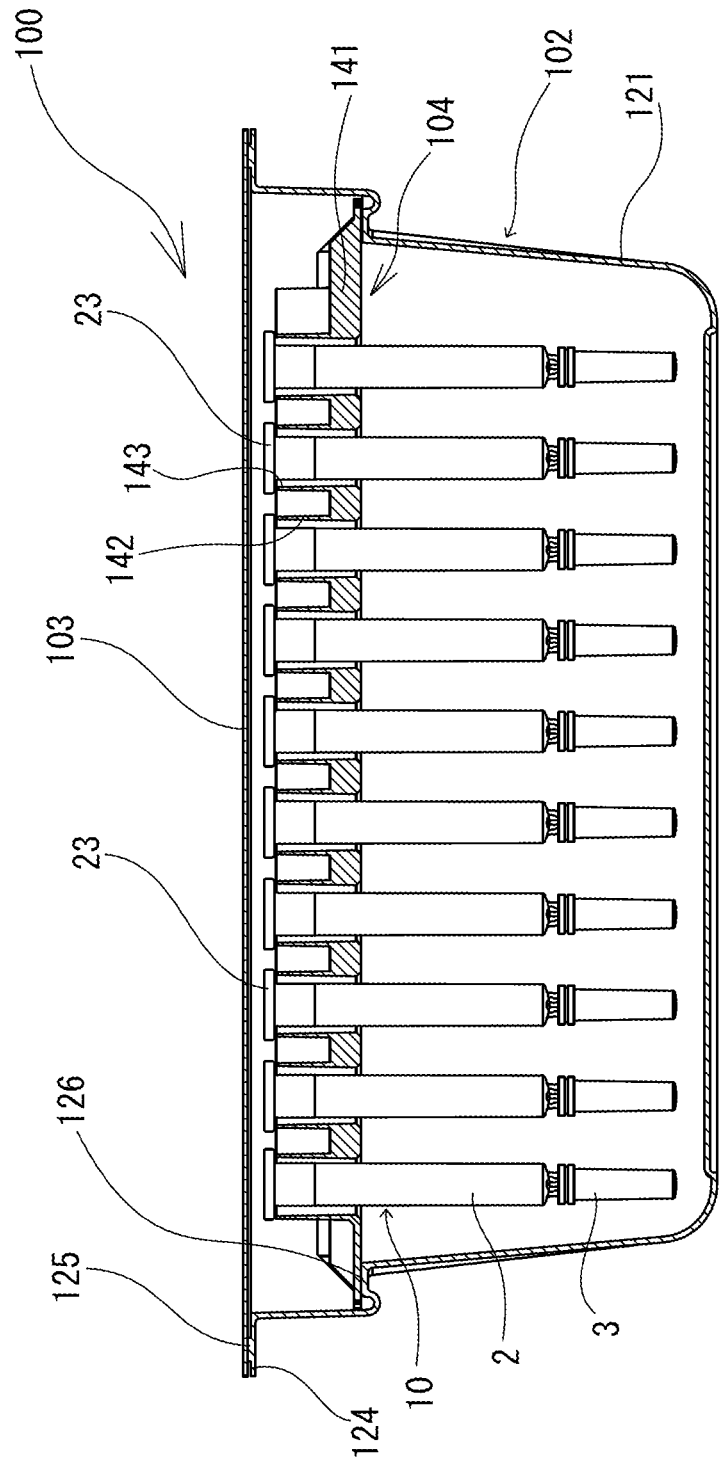

ASSEMBLY FOR SYRINGE, PREFILLED SYRINGE, SEAL CAP FOR BARREL AND PACKAGE FOR ASSEMBLY FOR SYRINGE

CROSS-REFERENCE TO RELATED PATENT APPLICATIONS

This application is a continuation application filed under 35 U.S.C. § 111(a) claiming the benefit under 35 U.S.C. §§ 120 and 365(c) of International Application No. PCT/JP2016/074275, filed on Aug. 19, 2016, which is based upon and claims the benefit of priority of Japanese Patent Application No. 2015-163245, filed on Aug. 20, 2015, the entireties of which are hereby incorporated by reference.

TECHNICAL FIELD

The present invention relates to an assembly for a syringe in which a seal cap is mounted on a barrel, a prefilled syringe, the seal cap for the barrel, and a package for the assembly for the syringe.

BACKGROUND ART

As a syringe for administering a small amount of a medical agent to a patient, a syringe having a piercing needle fixed to the distal end part of a barrel is used. In constructing a prefilled syringe in which the medical agent is filled in advance by using a syringe of this type, it is necessary to seal the tip of the syringe. Seal caps capable of sealing the tip of the syringe are proposed, as disclosed in a patent document 1 (Japanese Translation of PCT International Application Publication No. 2010-534546) and a patent document 2 (U.S. Pat. No. 6,719,732).

Prefilled syringes in which a medical agent has been filled in advance are used. But as apparent from a report that contents of many medical agents such as nitroglycerin, cyclosporine, benzodiazepines, and the like having a high degree of fat solubility decrease in various medical agent containers, interactions between injection solutions and medical appliances have become a problem. In consideration of this problem, as a material of a barrel for a syringe, resin such as cyclic polyolefin having a low degree of medicine adsorptive property has come to be used.

The present applicant proposed a prefilled syringe in which unlike the above-described needle-attached syringes, the barrel is sealed directly with the seal cap subjected to autoclave sterilization (Japanese Patent Application Laid-Open Publication No. 2005-319118: patent document 3).

PRIOR ART DOCUMENTS

Patent Documents

Patent document 1: Japanese Translation of PCT International Application Publication No. 2010-534546 (WO2009/016428, U.S. Pat. No. 8,939,941)
Patent document 2: U.S. Pat. No. 6,719,732
Patent document 3: Japanese Patent Application Laid-Open Publication No. 2005-319118

SUMMARY OF THE INVENTION

Problems to be Solved by the Invention

The seal cap (shield 10) of the patent document 1 covers the tip of the syringe (a part of the injection device is shown in FIG. 2 of patent document 1). The tip of the syringe 3 has the hub 2 to which the needle 6 is fixed. The shield 10 has the open proximal end 11, the closed tip 12, and the wall 13 extended from the proximal end 11 to the closed tip 12. The inner surface 14 of the wall 13 defines the cavity 15 accommodating a part of the tip of the syringe 3. For example, in a case where the shield 10 is fixed to the tip of the syringe to protect the tip while an injection device is being transported, the portion 14a of the inner surface 14 contacts the hub 2 disposed at the tip of the syringe 3.

In the seal cap (device for protecting the syringe needle) of the patent document 2, as shown in FIGS. 1 through 5 of the patent document 2, the elastic needle cap 20 extended longitudinally between the open proximal end 22 and the closed tip 24 has the inner housing 26 partitioned by the lateral direction wall 28 and the end wall 30. Between the first and second portions 40 and the second portion 42 of the housing 26, the annular bead (rib) 70 expanded inward is formed at the edge of the second portion 42 extended toward the proximal end 22. To improve the deformability of the annular bead 70 and facilitate the passing of the pressurized water vapor through the annular bead 70, four slots 72 longitudinally extended are formed on the bead 70.

As is often the case, the needle-attached prefillable syringe of this type is provided as the prefilled syringe in which a liquid medicine is filled. Thus, the seal cap having the function of sealing the needle tip of the barrel is mounted on the barrel. It is often the case that to seal the needle tip, the seal cap is formed by molding an elastic rubber material into which the needle tip can be pierced.

The above-described seal caps are required not to stick to the barrel with the seal caps being mounted on the barrel made of cyclic polyolefin after sterilization finishes and after the seal cap is stored for a predetermined period of time. The seal caps are also required to have satisfactory autoclave sterilization performance with the seal cap being mounted on the barrel.

It is an object of the present invention to provide a seal cap, for a barrel, which is required not to stick to the barrel after high-pressure steam sterilization which subjects the seal cap to a pressure load finishes and after the seal cap is stored for a predetermined period of time and have a satisfactory autoclave sterilization performance, even in a case where the barrel made of cyclic polyolefin is used, an assembly for a syringe using the seal cap for the barrel, a prefilled syringe, and a package for the assembly for the syringe.

Means for Solving the Problems

The above-described object can be achieved by the following form.

An assembly for a syringe comprises barrel having a barrel body having a distal end part and a seal cap mounted on said distal end part of said barrel, wherein said seal cap is formed of a thermoplastic elastomer composition containing as a main component thereof a mixture of a styrene-based thermoplastic elastomer and a softener for hydrocarbon-based rubber, said softener for hydrocarbon-based rubber has a kinematic viscosity of 1 to 5,000 $mm^2s^{-1}$ at 100 degrees C. and a naphthenic carbon ratio (% CN) of not more than 20% when said naphthenic carbon ratio is measured by ring analysis; and said barrel body of said barrel is formed of cyclic polyolefin.

The above-described object can be achieved by the following form.

A prefilled syringe comprises an assembly for a syringe according to the above assembly for a syringe, a gasket which is accommodated inside said barrel and liquid-tightly slidable inside said barrel, and a medical agent filled inside a space formed of said barrel and said gasket.

The above-described object can be achieved by the following form.

A seal cap for a barrel to be mounted on a distal end part of a barrel for a syringe, wherein said seal cap is formed of a thermoplastic elastomer composition containing as a main component thereof a mixture of a styrene-based thermoplastic elastomer and a softener for hydrocarbon-based rubber, said softener for hydrocarbon-based rubber has a kinematic viscosity of 1 to 5,000 $mm^2s^{-1}$ at 100 degrees C. and a naphthenic carbon ratio (% CN) of not more than 20% when said naphthenic carbon ratio is measured by ring analysis.

The above-described object can be achieved by the following form.

A package, for an assembly for a syringe, for accommodating a plurality of the above assemblies for syringes, said package comprising a container body whose upper surface is open and which has shape retainability, a barrel holding member capable of holding a plurality of said assemblies for syringes, a plurality of said assemblies for syringes held by said barrel holding member, and a sheet-shaped lid member which airtightly seals said open upper surface of said container body and is peelable therefrom, and an air-permeable part, having bacteria impermeability and sterilizing gas permeability, which is provided on said container body or on said sheet-shaped lid member, and said package accommodated a plurality of said assemblies for syringes was subjected to high-pressure steam sterilization.

BRIEF DESCRIPTION OF THE DRAWINGS

FIG. 19 is an enlarged sectional view taken along a line E-E of FIG. 18.

MODE FOR CARRYING OUT THE INVENTION

Figure 1:
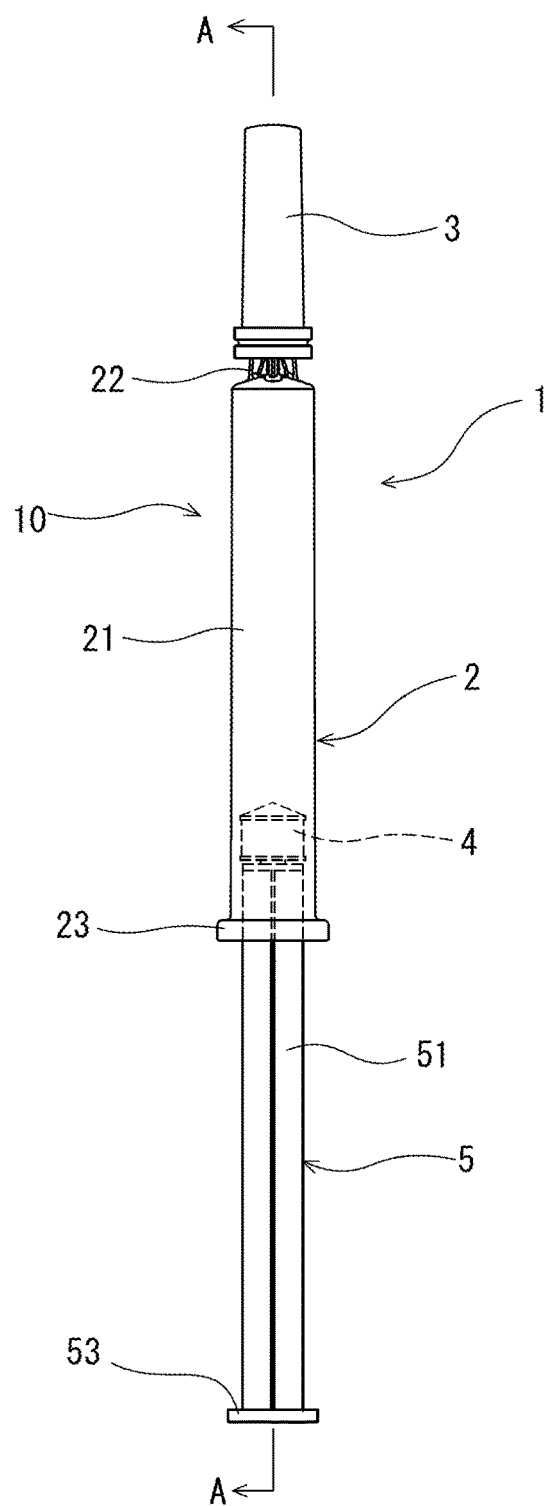
FIG. 1 is a front view of a prefilled syringe of an embodiment of the present invention.

By using the embodiments shown in the drawings, description is made below on a seal cap of the present invention for a barrel, an assembly, for a syringe, in which the seal cap has been mounted on the barrel, and a prefilled syringe using the assembly, for the syringe, in which the seal cap has been mounted on the barrel.

A prefilled syringe 1 of the present invention is composed of an assembly 10 for a syringe, a gasket 4 which is accommodated inside the assembly 10 for the syringe and liquid-tightly slidable inside the assembly 10 for the syringe, and a medical agent 8 filled inside a space formed of the assembly 10 for the syringe and the gasket 4.

The assembly 10 of the present invention for the syringe is composed of a barrel 2 having a barrel body 21 having a distal end part 22 and a seal cap 3 mounted on the distal end part 22 of the barrel 2. The seal cap 3 is formed of a thermoplastic elastomer composition containing as its main component a mixture of a styrene-based thermoplastic elastomer and a softener for hydrocarbon-based rubber, the softener for hydrocarbon-based rubber has a kinematic viscosity of 1 to 5,000 $mm^2s^{-1}$ at 100 degrees C. and a naphthenic carbon ratio (% CN) of not more than 20% when the naphthenic carbon ratio is measured by ring analysis; and the barrel body of said barrel is formed of cyclic polyolefin.

The assembly 10 for the syringe (in other words, piercing needle-attached barrel on which cap is mounted) shown in the drawings is composed of the barrel 2 having the barrel body 21 having a piercing needle fixing portion provided at the distal end part 22 and a piercing needle 6 which has a piercing needle tip 61 at its distal end and whose proximal end portion is fixed to the piercing needle fixing portion and the seal cap 3 mounted on the barrel 2.

The seal cap 3 shown in the drawings has a closed distal end part 31, an open proximal end part 32, a cylindrical hollow part 30 extended from the open proximal end part 32 toward a distal end of the seal cap and being capable of accommodating the distal end part (piercing needle fixing portion) 22 therein, and a pierceable part 33 into which the piercing needle tip 61 of the piercing needle 6 inserted into the hollow part 30 is pierceable. In the assembly 10 of this embodiment for the syringe, the seal cap 3 is mounted on the barrel 2. The seal cap 3 has the pierceable part 33 into which the piercing needle tip 61 of the piercing needle 6 is pierceable, so that the assembly 10 has a state in which the piercing needle tip 61 is pierced into the pierceable part 33 thereof.

Figure 2:
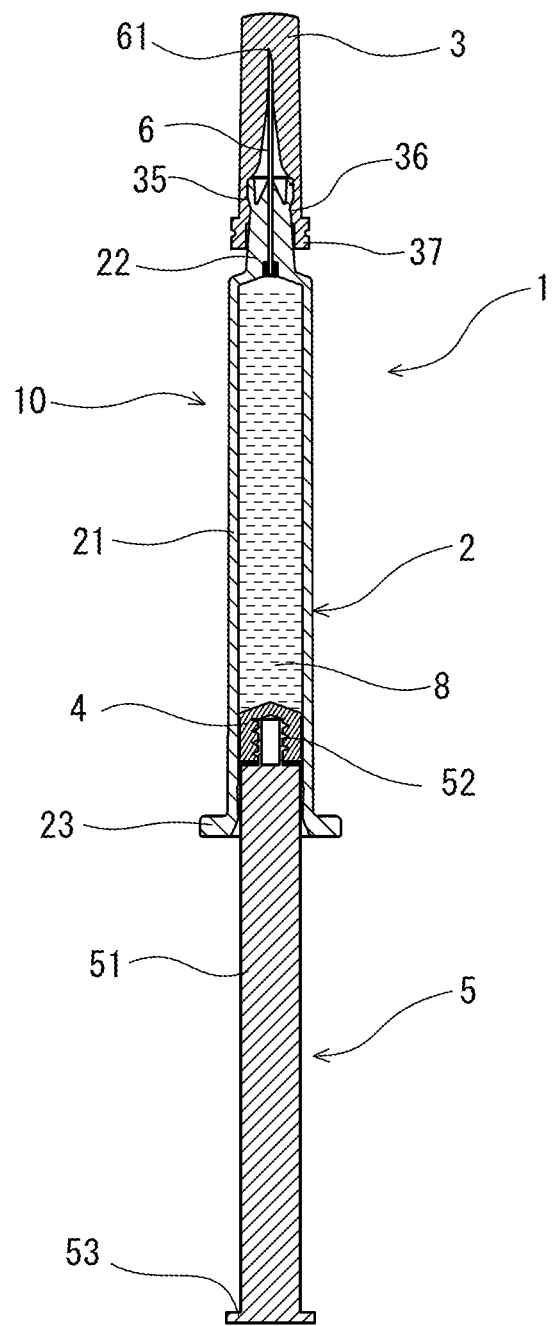
FIG. 2 is a sectional view taken along a line A-A of FIG. 1.

As shown in FIGS. 1 and 2, the prefilled syringe 1 is composed of the assembly 10, for the syringe, which consists of the barrel 2 and the seal cap 3 mounted on the barrel 2 so as to seal the needle tip 61 of the piercing needle 6, the gasket 4 which is accommodated inside the assembly 10 for the syringe and liquid-tightly slidable inside the assembly 10 for the syringe, the medical agent 8 filled inside the space formed of the assembly 10 for the syringe and the gasket 4, and a plunger 5 mounted on the gasket 4 in advance or when the prefilled syringe is used.

The medical agent 8 is filled inside the space formed of the barrel 2, the gasket 4, and the seal cap 3.

As the medical agent 8 to be filled inside the above-described space, it is possible to use any medical agent to be used as injection solutions. Examples of the medical agent include protein pharmaceuticals such as an antibody, peptide pharmaceuticals such as hormone, nucleic acid medicines, cell medicines, blood products, vaccines for protecting infectious diseases, anticancer drugs, anesthetics, jolt, antibiotics, steroid drugs, proteolytic enzyme inhibitor, heparin, sugar injections such as glucose, an electrolyte correction injection solution such as sodium chloride, potassium lactate, and the like, vitamin preparations, fat emulsion, an imaging agent, and a stimulant drug.

The barrel 2 has the barrel body 21, the cylindrical (hollow) distal end part (piercing needle fixing portion) 22 provided at the distal end side of the barrel body 21, a flange 23 provided at a proximal end portion of the barrel body 21, and the piercing needle 6 whose proximal end portion is fixed to the distal end part (piercing needle fixing portion) 22.

The piercing needle 6 has the piercing needle tip 61 at its distal end. The proximal end portion of the piercing needle 6 is inserted into a hollow portion of the distal end part (piercing needle fixing portion) 22 and fixed thereto with the inside of the piercing needle 6 communicating with an inner space 20 of the barrel 2. In other words, the piercing needle 6 is embedded in the distal end part 22 of the barrel 2 at a portion thereof disposed a little distally from the proximal end (proximal end portion of piercing needle not including proximal end) thereof. Thus, the hollow portion of the distal end part 22 is unrecognizable. As the piercing needle 6, a metallic hollow needle having its tip at its distal end is used. In this embodiment, a lubricant is applied to at least the piercing needle tip 61 of the piercing needle 6. Although the kind of the lubricant is not limited to a specific one, silicone oil is used in this embodiment. By using the silicone oil, it is possible to expect a decrease in the piercing resistance of the piercing needle tip at a piercing time.

The piercing needle 6 may be inserted into the hollow portion of the distal end part 22 of the barrel 2 formed by molding a material in advance and fixed to the distal end part 22 by means of an adhesive agent, thermal welding or the like. The piercing needle 6 may be fixed to the barrel 2 by insert molding. In the case of the insert molding, by forming the barrel 2 by molding the material, the distal end part 22 has a cylindrical (hollow) configuration into which the piercing needle 6 has been inserted. More specifically, the proximal end portion of the piercing needle 6 is inserted into the hollow portion of the distal end part 22 and fixed thereto.

Figure 7:
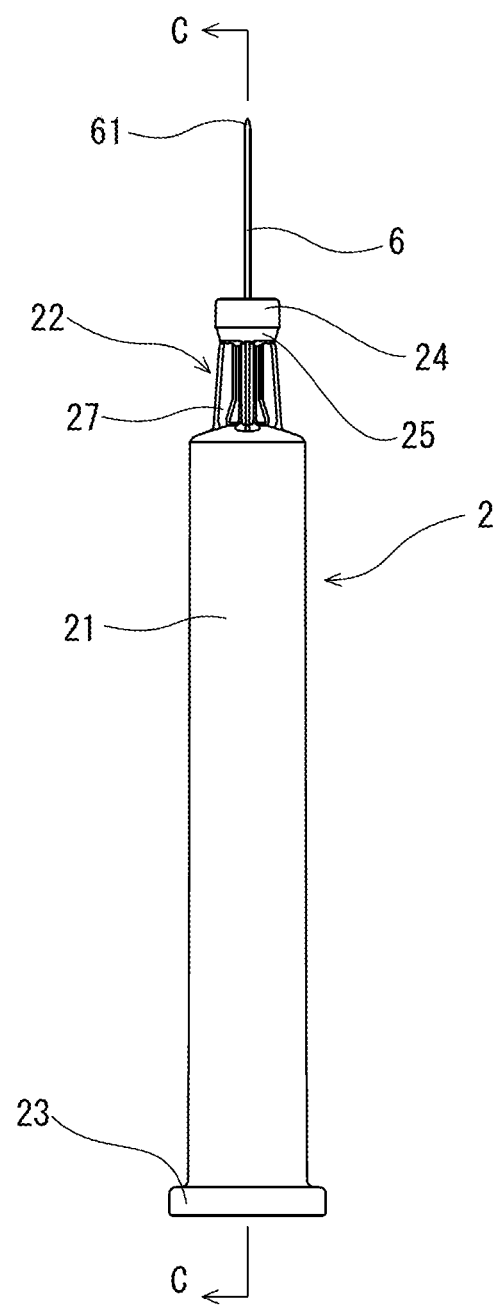
FIG. 7 is a front view of the barrel for use in the prefilled syringe shown in FIGS. 1 and 2 and the assembly for the syringe shown in FIG. 3.
Figure 8:
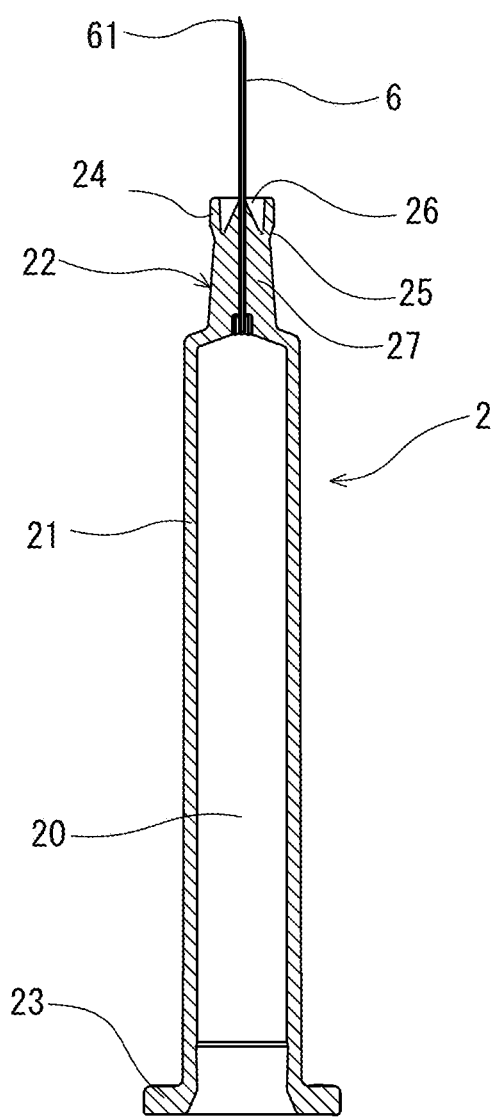
FIG. 8 is an enlarged sectional view taken along a line C-C of FIG. 7.

The barrel 2 is transparent or semitransparent. The barrel body 21 is a substantially cylindrical part which accommodates the gasket 4 liquid-tightly and slidably. The distal end part 22 is a hollow cylindrical part projecting forward from the distal end of the barrel body and having a smaller diameter than the barrel body. As shown in FIGS. 7 and 8, the distal end part 22 has a head portion 24 provided at its distal end, a short tapered diameter-decreased portion 25 which is provided at the proximal end of the head portion 24 and becomes shorter toward its proximal end in its diameter, and a connecting portion 27 connecting a proximal end portion of the tapered diameter-decreased portion 25 and the distal end of the barrel body 21 to each other. A concave portion is formed of the tapered diameter-decreased portion 25. In the head portion 24, there are formed a concavity 26 recessed from a distal end surface of the head portion 24 toward its proximal end and a hollow conical portion which is positioned inside the concavity 26 and has an apex at the distal end side of the head portion 24.

A plurality of grooves extended in the axial direction of the barrel 2 is formed on an outer surface of the connecting portion 27. It is possible that the concave portion 25 does not have a tapered configuration, but has a diameter-decreased configuration so that the concave portion 25 is stepped from the proximal end of the head portion 24. In addition, it is possible to omit the formation of the connecting portion 27 and directly connect the proximal end portion of the concave portion (tapered diameter-decreased portion 25) and the distal end of the barrel body 21 to each other. It is also possible to omit the formation of the concavity 26 and the conical portion and form the head portion 24 into a hollow and columnar (cylindrical) configuration. It is preferable to form the concave portion 25 annularly as in the case of this embodiment.

As a material for forming the barrel 2, cyclic polyolefin is used. As the cyclic polyolefin, it is possible to use both a cyclic olefin polymer (COP) which is a homopolymer of cyclic olefin and a cyclic olefin copolymer (COC). As the cyclic polyolefin, it is possible to use a ring-opening metathesis polymer of a cyclic olefin monomer, a cyclic olefin polymer (COP) comprising a ring-opening metathesis polymer of cyclic olefin monomer and its hydrogenated product, a copolymer of the cyclic olefin and olefin, and a cyclic olefin copolymer (COC) consisting of a copolymer of the cyclic olefin monomer and α-olefin.

As the piercing needle 6, a hollow needle having the piercing needle tip 61 at its distal end is used. As a material for forming the piercing needle 6, metals are normally used. Of metals, stainless steel is preferable.

As shown in FIGS. 1 and 2, the gasket 4 has a body part extended in substantially an equal diameter and a plurality of annular ribs (although two annular ribs are formed in this embodiment, not less than two annular ribs may be appropriately formed, provided that the rib satisfies liquid tightness and slidability) formed on the body part. The ribs liquid-tightly contact the inner surface of the barrel 2. A distal end surface of the gasket 4 has a configuration corresponding to that of the inner surface of the distal end of the barrel 2 to prevent the formation of a gap between both surfaces as much as possible when both surfaces contact each other.

As a material for forming the gasket 4, it is preferable to use elastic rubber (for example, isoprene rubber, butyl rubber, latex rubber, silicone rubber, and the like); and synthetic resin (for example, styrene elastomer such as SBS elastomer, SEBS elastomer, and the like and olefin elastomer such as ethylene-α-olefin copolymer elastomer).

The gasket 4 has a concave portion extended inward from its proximal end portion. The concave portion of the gasket 4 is female screw-shaped and threadedly engageable with a male screw portion formed on an outer surface of a projected portion 52 formed at a distal end portion of the plunger 5. Threaded engagement between the female and male screw portions prevents the plunger 5 from being removed from the gasket 4. The plunger 5 may be removed from the gasket when the prefilled syringe is not used and mounted thereon when the prefilled syringe is used. The plunger 5 has the projected portion 52 projected forward tubularly from a disk portion disposed at its distal end. The male screw which threadedly engages the concave portion of the gasket 4 is formed on an outer surface of the projected portion. The plunger 5 has a body part 51 cross-shaped in its cross section and axially extended and a pressing disk portion 53 provided at its proximal end portion.

The seal cap 3 of the present invention for the barrel is used by mounting the seal cap on the barrel having the barrel body 21, the cylindrical distal end part (piercing needle fixing portion) 22 provided at the distal part of the barrel body 21 and having the head portion 24, and the piercing needle 6 which has the piercing needle tip 61 at its distal end and the proximal end portion of which is inserted into the distal end part 22 and fixed thereto.

Figure 3:
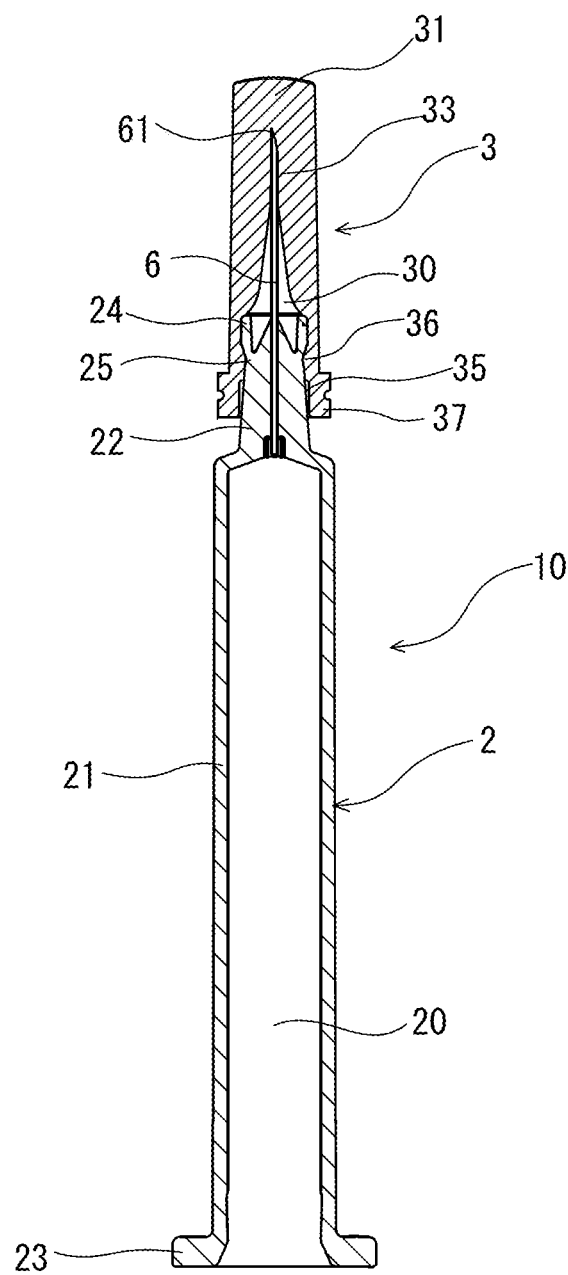
FIG. 3 is an enlarged sectional view of an assembly of the present invention for a syringe for use in the prefilled syringe shown in FIGS. 1 and 2.
Figure 6:
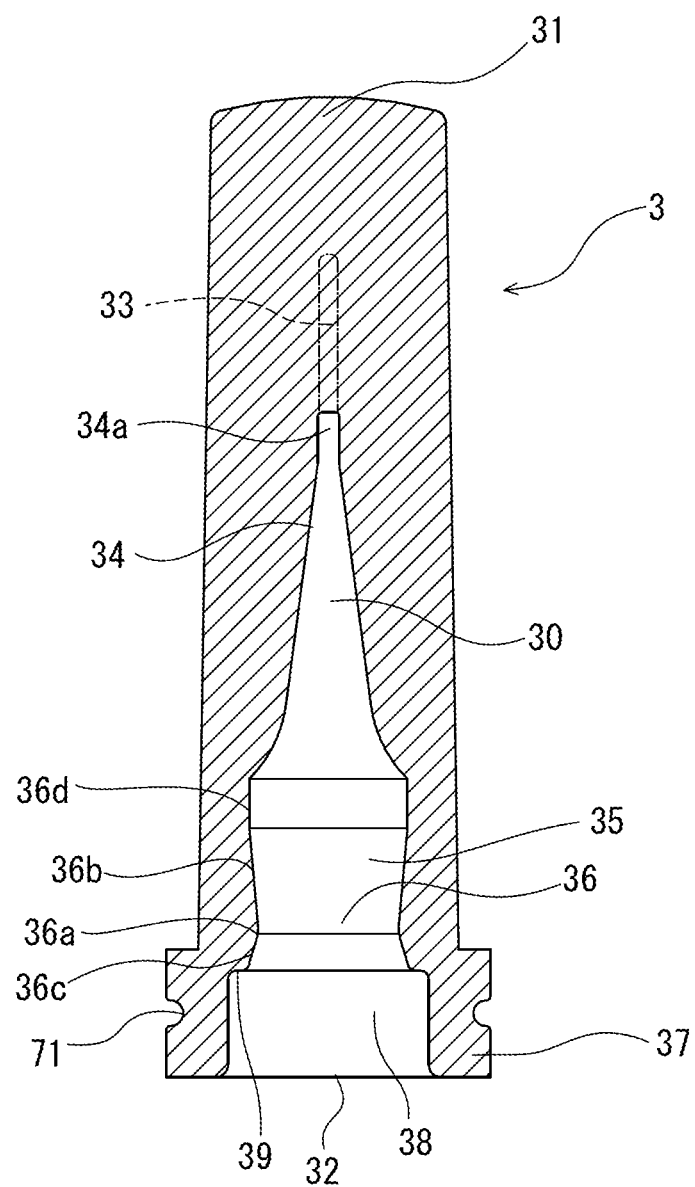
FIG. 6 is an enlarged sectional view taken along a line B-B of FIG. 4.

As shown in FIG. 6, the seal cap 3 has the closed distal end part 31, the open proximal end part 32, and the hollow part 30 extended from the open proximal end part 32 toward the distal end of the seal cap. The hollow part 30 has a piercing needle fixing portion accommodating part 35 accommodating the distal end part 22 at its proximal end portion and a tapered piercing needle accommodating part 34 continuous with the distal end of the piercing needle fixing portion accommodating part 35. Furthermore, the seal cap has the pierceable part 33 into which the piercing needle tip 61 of the piercing needle 6 accommodated inside the piercing needle accommodating part 34 can be pierced and a projected part 36 formed on the inner surface of the piercing needle fixing portion accommodating part 35. As shown in FIG. 3, in the seal cap 3 of this embodiment mounted on the barrel 2, at least a part of the hollow part 30 (more specifically, the piercing needle fixing portion accommodating part 35 which is a part of the hollow part and the vicinity thereof) is expansively spread outward by the distal end part 22 accommodated inside the hollow part 30.

The seal cap 3 is formed of the thermoplastic elastomer composition containing as its main component the mixture of the styrene-based thermoplastic elastomer and the softener, for the hydrocarbon-based rubber, which has the kinematic viscosity of 1 to 5,000 $mm^2s^{-1}$ at 100 degrees C. and contains not more than 20% of the naphthenic carbon when the content ratio (% CN) of the naphthenic carbon is measured by ring analysis. Thus, when the seal cap is stored in a state where the seal cap is in contact with the piercing needle, the material of the seal cap does not attach to the piercing needle. The thermoplastic elastomer composition used for the seal cap is an elastic thermoplastic resin composition. "The mixture of the styrene-based thermoplastic elastomer and the softener for the hydrocarbon-based rubber is contained as the main component" of the thermoplastic elastomer composition for use in the seal cap 3 means that the total amount of the styrene-based thermoplastic elastomer and the softener for the hydrocarbon-based rubber is not less than 50 percentage by weight of the entire thermoplastic elastomer composition.

It is preferable that the styrene-based thermoplastic elastomer consists of a styrene-based block copolymer. It is preferable that the styrene-based block copolymer consists of a block copolymer having at least one polymer block P containing a vinyl aromatic compound as its main component and at least one polymer block Q containing conjugated diene as its main component, a hydrogenated block copolymer to be obtained by hydrogenating the block copolymer or a mixture of the above-described block copolymer and the above-described hydrogenated block copolymer.

More specifically, it is possible to exemplify a styrene-isoprene-butadiene-styrene block copolymer (SIBS), a hydrogenated styrene-isoprene-butadiene-styrene block copolymer, a styrene-ethylene-propylene-styrene block copolymer (SEPS), a styrene-butadiene copolymer (SB), a styrene-butadiene-styrene block copolymer (SBS), a hydrogenated styrene-butadiene-styrene block copolymer, a styrene-isoprene-styrene block copolymer (SIS), a styrene-ethylene-butene copolymer (SEB), a styrene-ethylene-propylene copolymer (SEP), a styrene-isobutylene-styrene block copolymer, and mixtures consisting of one or not less than two kinds of the above-described copolymers. A styrene-ethylene-ethylene-propylene-styrene block copolymer (SEEPS) is especially preferable.

It is more favorable that the styrene-based thermoplastic elastomer consists of a block copolymer having at least one polymer block P containing a vinyl aromatic compound as its main component and at least one polymer block Q containing conjugated diene and/or isobutylene as its main component or a hydrogenated block copolymer to be obtained by hydrogenating the block copolymer. "Contained as the main component" in the block copolymer means that both the content of the vinyl aromatic compound of the block P and the content of the conjugated diene and/or the isobutylene of the block Q are not less than 50 percentage by weight respectively.

The thermoplastic elastomer composition may contain thermoplastic resin other than the styrene-based thermoplastic elastomer. As the thermoplastic resin to be used for the thermoplastic elastomer composition, polyolefin and the like are preferable. As the polyolefin, polypropylene and polyethylene are preferable.

The softener for the hydrocarbon-based rubber to be contained in the thermoplastic elastomer composition to be used in the present invention has a kinematic viscosity of 1 to 5,000 $mm^2s^{-1}$ and contains the naphthenic carbon at a content ratio (% CN) not more than 20% when the content ratio thereof is measured by the ring analysis. The softener, for the hydrocarbon-based rubber, which has the above-described properties is highly compatible with the thermoplastic resin. In addition, the thermoplastic elastomer composition containing the softener for the hydrocarbon-based rubber has a low degree of permeability into the cyclic polyolefin to be used to form the barrel body.

As the softener for the hydrocarbon-based rubber, an ethylene-α-olefin copolymer, polybutene, and paraffinic oil, and the like are exemplified. The softener for the hydrocarbon-based rubber may be used in combination of different kinds of softeners.

As the ethylene-α-olefin copolymer, the ethylene-α-olefin copolymer which is a copolymer of ethylene and an α-olefin copolymer whose carbon number is 1 to 10 is more favorable. An ethylene-propylene copolymer is especially favorable. The ethylene-propylene copolymer may be composed of ethylene and the α-olefin other than propylene.

From the standpoint of the moldability of the thermoplastic elastomer composition, the kinematic viscosity (JIS K2283) of the softener for the hydrocarbon-based rubber at 100 degrees C. is favorably 1 to 5,000 $mm^2s^{-1}$, more favorably 10 to 4,000 $mm^2s^{-1}$, and most favorably 20 to 3,000 $mm^2s^{-1}$.

From the standpoint of prevention of the permeation of the softener for the hydrocarbon-based rubber into the cyclic polyolefin, the softener for the hydrocarbon-based rubber has a naphthenic carbon ratio (%CN) of not more than 20%, more favorably at the naphthenic carbon ratio of not more than 15%, and most favorably at the naphthenic carbon ratio of not more than 10%, when the naphthenic carbon ratio is measured by ring analysis. The naphthenic carbon ratio (%CN) is percentage of naphthene carbon in whole number of carbon atoms. The naphthene carbon ratio (%CN) is a ratio of the number of naphthenic carbon atoms of the softener in the whole number of carbon atoms of the softener. The softener for the hydrocarbon-based rubber has an aromatic carbon ratio (%CA) of not more than 5% favorably, and more favorably at a ratio of not more than 1% when the aromatic carbon ratio is measured by ring analysis. The aromatic carbon ratio (%CA) is percentage of naphthene carbon in whole number of carbon atoms. The aromatic carbon ratio (%CA) is a ratio of the number of aromatic carbon atoms of the softener in the whole number of carbon atoms of the softener. The ring analysis can be conducted by an n-d-M method prescribed in the ASTM D2140 or the ASTM D3238.

The content of the softener for the hydrocarbon-based rubber contained in the thermoplastic elastomer composition is set to favorably 20 to 70 percentage by weight, more favorably 30 to 60 percentage by weight, and most favorably 35 to 50 percentage by weight. The addition amount of the softener for the hydrocarbon-based rubber for 100 parts by weight of the styrene-based thermoplastic elastomer (when not less than two kinds of the styrene-based thermoplastic elastomers are used, the addition amount means the total of a plurality of styrene-based thermoplastic elastomers) contained in the thermoplastic elastomer composition is set to favorably 30 to 300 parts by weight and more favorably 50 to 200 parts by weight.

The material for forming the seal cap of the present invention may contain a release agent. The amount of the release agent is set to favorably 0.03 to 5 parts by weight and more favorably 0.05 to 3 parts by weight for 100 parts by weight of a base polymer. As the release agent, it is possible to list high fatty acid amide such as erucic acid amide, stearic acid amide, oleic acid amide, palmitic acid amide; high fatty acid ester such as ethyl oleate; high fatty acid amine such as stearylamine and oleylamine; ester of aliphatic alcohol; paraffin (paraffin corresponding to ethylene-α-olefin copolymer is excluded when it is used as a release agent), and silicone oil. But the release agent to be used for the seal cap of the present invention is not limited to the above-described ones.

The material for forming the seal cap of the present invention may contain a pigment such as carbon black, titanium oxide, and the like as a colorant as necessary. The material for the seal cap of the present invention may contain a filler such as an inorganic filler, for example, talc, calcium carbonate, zinc carbonate, wollastonite, silica, alumina, magnesium oxide, calcium silicate, sodium aluminate, calcium aluminate, sodium aluminosilicate, magnesium silicate, glass balloon, carbon black, zinc oxide, antimony trioxide, zeolite, hydrotalcite, metal fibers, metal whiskers, ceramic whiskers, potassium titanate, boron nitride, and carbon fibers; and an organic filler such as naturally derived polymers, for example, starch, fine cellulose particles, wood flour, tofu refuse, chaff, and wheat bran and denatured products of these polymers.

The inner surface of the piercing needle fixing portion accommodating part 35 of the seal cap 3 and the outer surface of the distal end part 22 of the barrel 2 are in close contact with each other.

As shown in FIG. 3, the assembly 10 of the present invention for the syringe has a state in which the seal cap 3 is mounted on the distal end part (piercing needle fixing portion) 22 of the barrel 2, with the piercing needle tip 61 of the piercing needle 6 being pierced into the pierceable part 33 of the seal cap 3 and sealed liquid-tightly, with the concave portion 25 positioned proximally from the head portion 24 of the distal end part 22 and the projected part 36 formed on the inner surface of the piercing needle fixing portion-accommodating part 35 engaging each other, and with the inner surface of the piercing needle fixing portion-accommodating part 35 and the outer surface of the distal end part 22 in close contact with each other. As shown in FIG. 3, in the seal cap 3 of this embodiment mounted on the barrel 2, at least a part of the hollow part 30 (more specifically, the piercing needle fixing portion accommodating part 35 which is a part of the hollow part and the vicinity thereof) is expansively spread outward by the distal end part 22 accommodated inside the hollow part 30.

As shown in FIG. 3, the assembly 10 of the present invention for the syringe has a state in which the seal cap 3 is mounted on the distal end part (piercing needle fixing portion) 22 of the barrel 2, with the piercing needle tip 61 of the piercing needle 6 being pierced into the pierceable part 33 of the seal cap 3 and sealed liquid-tightly, with the concave portion 25 (proximal end portion of the head portion 24) of the distal end part 22 and the projected part 36 formed on the inner surface of the piercing needle fixing portion-accommodating part 35 engaging each other, and with the inner surface of the piercing needle fixing portion-accommodating part 35 and the outer surface of the distal end part 22 in close contact with each other. At this time, at least the piercing needle fixing portion accommodating part 35 is placed in a state in which it is expansively spread outward by the distal end part 22.

The form of the inner surface of the seal cap 3 of this embodiment is described below.

The seal cap 3 has the projected part 36, formed on the inner surface thereof, which is located at a position distal from the open proximal end part 32 at a predetermined length. The projected part 36 has an apex 36a projected to a highest extent and an inclined portion (tapered portion) 36b which is extended from the apex 36a toward the distal end of the seal cap and becomes gradually lower in its projection height toward the distal end of the seal cap. In this embodiment, the projected part 36 is formed as an annular projected part. The inclined portion 36b is formed as a tapered portion in such a way that the inner diameter of the piercing needle fixing portion accommodating part 35 decreases toward the distal end of the seal cap.

The inner diameter of the piercing needle fixing portion accommodating part 35 at the apex 36a is set a little smaller than the outer diameter of the head portion 24 of the distal end part 22 of the barrel 2. Thereby when the seal cap 3 is mounted on the distal end part 22 of the barrel 2, the piercing needle fixing portion accommodating part 35 which forms a part of the hollow part and its vicinity are expansively spread outward by the distal end part 22 accommodated inside the hollow part 30, as shown in FIG. 3.

Thereby the inner surface of the piercing needle fixing portion accommodating part 35 of the seal cap 3 is pressed against the outer surface of the head portion 24 with both surfaces in close contact with each other. Further, in this embodiment, the projected part 36 and the concave portion 25 are in engagement with each other. In a state where the seal cap 3 is mounted on the distal end part 22 of the barrel 2, the distal end side inclined portion 36b is extended toward the distal end of the seal cap beyond the concave portion 25. The inner diameter of the piercing needle fixing portion accommodating part 35 at at least the distal end portion of the distal end side inclined portion 36b is a little smaller than the outer diameter of the head portion 24 of the distal end part 22 of the barrel 2.

Figure 9:
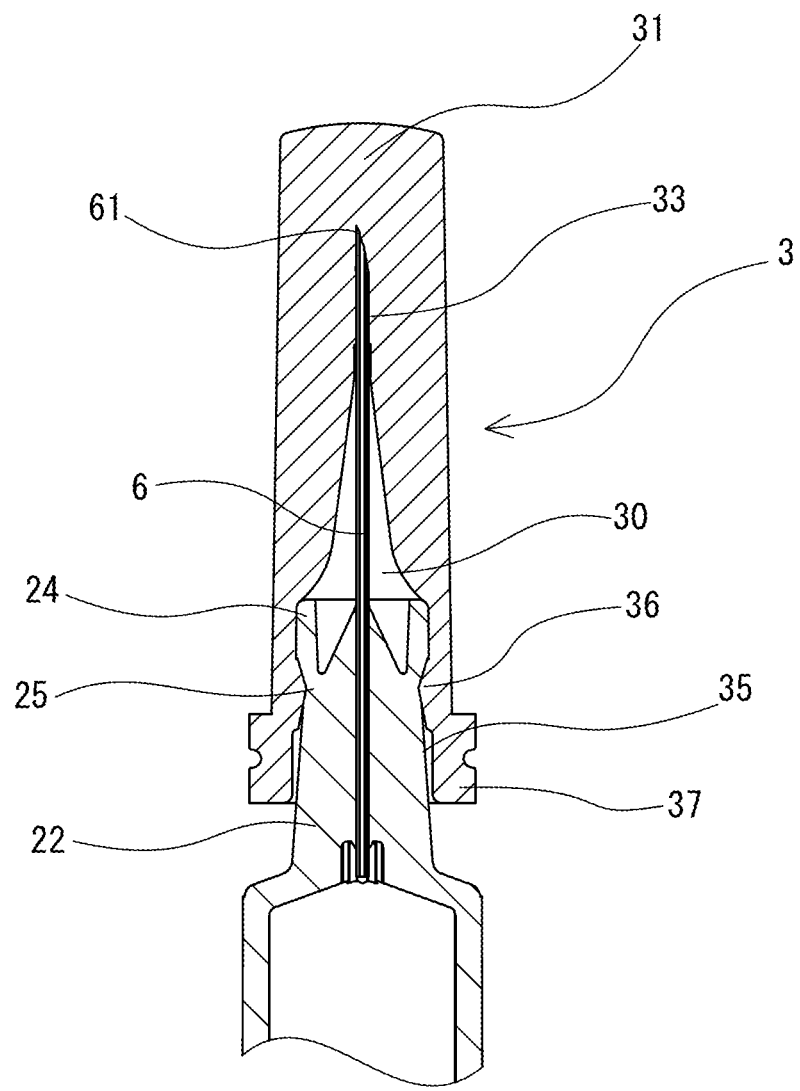
FIG. 9 is an enlarged sectional view of a distal end part of the assembly for the syringe shown in FIG. 3.
Figure 10:
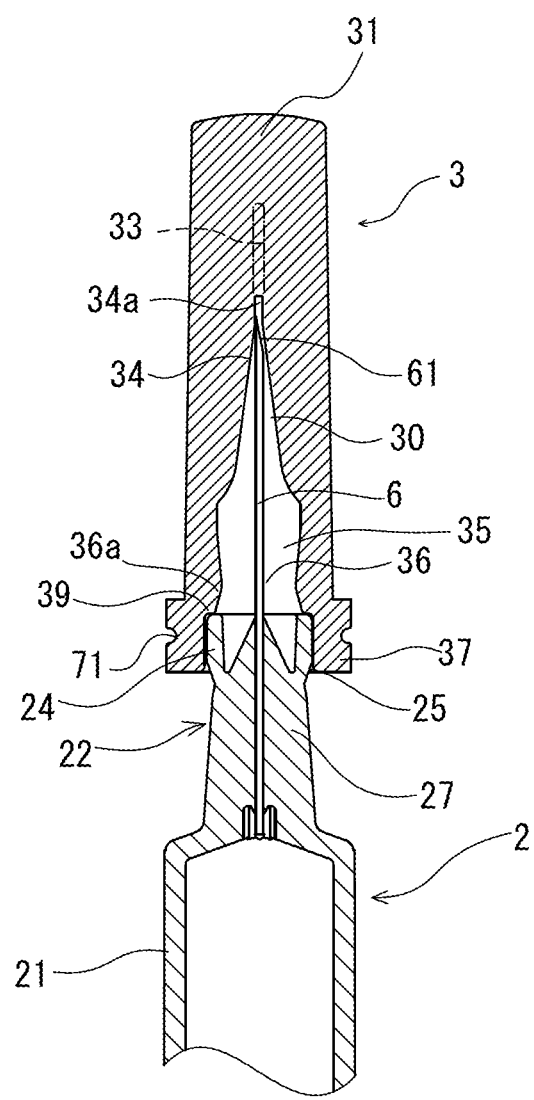
FIG. 10 is an explanatory view for explaining the action of the seal cap of the present invention for use in the barrel.

Thereby as shown in FIGS. 9 and 10, when the seal cap 3 is mounted on the distal end part 22 of the barrel 2, the inner surface of the distal end side inclined portion 36b is entirely pressed against the outer surface of the head portion 24 with both surfaces in close contact with each other. Thereby it is possible to reduce undesired removal of the seal cap 3 from the barrel 2 to a higher extent. Further, because the distal end side inclined portion 36b is pressed against the outer surface of the head portion 24, at least the piercing needle fixing portion accommodating part 35 is placed in a state in which it is expansively spread outward by the heat portion 24.

In the seal cap 3 of this embodiment, as shown in FIG. 6, the projected part 36 further includes a proximal end side inclined portion 36c which extends from the apex 36a toward an open end (proximal end) of the seal cap and gradually decreases in its projection height toward the open end (proximal end) of the seal cap. Thereby in mounting the seal cap 3 on the distal end part 22 of the barrel 2, the apex 36a of the projected part 36 is capable of easily climbing over the head portion 24 of the distal end part 22 from the distal end side of the head portion 24.

In the seal cap 3 of this embodiment, the piercing needle fixing portion accommodating part 35 has a linear portion 36d extended at a predetermined length (more specifically, extended to the proximal end portion of the piercing needle accommodating part 34) from a distal end portion of the distal end side inclined portion 36b of the projected part 36 toward the distal end of the seal cap. The inner diameter of the piercing needle fixing portion accommodating part 35 at the linear portion 36d thereof is constant and a little smaller than the outer diameter of the head portion 24 of the distal end part 22 of the barrel 2. Thereby when the seal cap 3 is mounted on the distal end part 22 of the barrel 2, the linear portion 36d is pressed against the outer surface of the head portion 24 with the linear portion 36d in close contact with the outer surface of the head portion 24. Because the linear portion 36d is pressed against the outer surface of the head portion 24, at least the piercing needle fixing portion accommodating part 35 is placed in the state in which it is expansively spread outward by the heat portion 24.

In this embodiment, the proximal end portion of the distal end side inclined portion 36b of the projected part 36 of the seal cap 3 is positioned on the periphery of the concave portion 25 of the distal end part 22 of the barrel 2. The inner diameter of the piercing needle fixing portion accommodating part 35 in the vicinity of at least the proximal end portion of the distal end side inclined portion 36b is a little smaller than the outer diameter of the annular concave portion 25. Thereby, the distal end side inclined portion 36b of the projected part 36 of the seal cap 3 is pressed against the outer surface of the concave portion 25 with the distal end side inclined portion 36b in close contact with the outer surface of the concave portion 25. Thereby it is possible to reduce undesired removal of the seal cap 3 from the barrel 2 to a higher extent.

In this embodiment, the concave portion 25 consists of the tapered diameter-decreased portion which is provided at the proximal end side of the head portion 24 and decreases toward the proximal end of the barrel in its diameter. Thereby in removing the seal cap 3 from the barrel 2, the projected part 36 of the seal cap 3 is expansively spread outward along the concave portion 25 and is thus capable of easily climbing over the head portion 24.

In the seal cap 3 of this embodiment, the hollow part 30 has a piercing needle fixing portion-introducing portion 38 which is formed in a range from the open proximal end part 32 of the seal cap 3 to the proximal end of the piercing needle fixing portion accommodating part 35 (projected part 36) and is extended in a substantially equal inner diameter.

The piercing needle fixing portion-introducing portion 38 has an inner diameter a little larger than a maximum inner diameter of the piercing needle fixing portion accommodating part 35 and a little larger than the outer diameter of the head portion 24 of the distal end part 22 of the barrel 2. Therefore, in mounting the seal cap 3 on the piercing needle fixing portion 22 of the barrel 2, the piercing needle fixing portion-introducing portion 38 functions as a portion for introducing the piercing needle fixing portion 22 into the seal cap.

The piercing needle fixing portion-introducing portion 38 has an annular erect surface 39 erect toward the open proximal end part 32 at a boundary between the piercing needle fixing portion-introducing portion 38 and the proximal end of the piercing needle fixing portion accommodating part 35 (projected part 36). Thus, when the distal end part of the barrel 2 is inserted into the piercing needle fixing portion-introducing portion 38 of the seal cap 3, the piercing needle fixing portion 22 of the barrel 2 enters the piercing needle fixing portion-introducing portion 38. Thereafter as shown in FIG. 10, an annular distal end surface of the head portion 24 of the piercing needle fixing portion 22 contacts the annular erect surface 39. In this state, the piercing needle 6 becomes substantially parallel with the central axis of the seal cap 3 and enters the small-diameter distal end portion 34a of the piercing needle accommodating part 34.

A gripping flange 37 is formed at the proximal end portion of the seal cap 3 by projecting the flange 37 outward and annularly. An annular concave portion 71 is formed on the flange 37. The distal end position of the flange 37 is positioned distally from the annular erect surface 39 of the hollow part 30 and in the vicinity of the apex 36a of the projected part 36 (in the case of the flange shown in FIG. 6, the distal end position of the flange is located at a position a little proximal from the apex 36a, namely, at the side of the open portion).

The seal cap of the present invention may be exposed to a high concentration ozone environment before it is used. The high concentration ozone environment includes a static electricity removal environment adopting a corona discharge method, the inside of an ozone sterilizer, inside a clean room where ozone sterilization is performed, and a space (for example, hospital) in which an air cleaner generating ozone is used.

When the seal cap and the barrel on which the seal cap has been mounted are charged with static electricity, the seal cap and the barrel may adsorb dust and the like during production processes. Therefore, the production processes are performed in the static electricity removal environment from which the static electricity is removed. The static electricity removal environment can be formed by introducing ions generated by using an ionizer adopting the corona discharge method into the production processes together with pure air.

At a corona discharge time, ions and ozone are generated. As a result, the barrel on which the seal cap has been mounted contacts the ozone. But because the seal cap of the present invention mounted on the barrel is made of the above-described material, the seal cap is not deteriorated by the ozone. Therefore, it hardly occurs that the seal cap deteriorates owing to contact between the seal cap and the ozone. The method to be used to form the static electricity removal environment is not limited to the corona discharge method (both voltage application method and self-discharge method can be used), but it is possible to use an AC discharge method, a DC discharge method or a pulse discharge method.

A prefilled syringe 40 and an assembly 50 for a syringe of another embodiment of the present invention are described below with reference to FIGS. 11 through 13.

The prefilled syringe 40 of the present invention is composed of the assembly 50 for the syringe, a gasket 42 which is accommodated inside the assembly 50 for the syringe and liquid-tightly slidable inside the assembly 50 for the syringe, and a medical agent 41 filled inside a space formed of the assembly 50 for the syringe and the gasket 42.

The assembly 50 for the syringe is composed of a barrel 80 and a seal cap 90 for sealing an open distal end part of the barrel 80. The barrel 80 has a barrel body part 81, a distal end part (nozzle part) 82 provided at a distal end side of the barrel body part 81 and having an open portion at its distal end, and an outwardly projected flange 84 provided at a rear end side of the barrel body part 81.

The prefilled syringe 40 of this embodiment is composed of the barrel 80, a sealing member 90 for sealing the distal end part 82 of the barrel 80, the gasket 42 which is accommodated inside the barrel and slidable inside the barrel, a plunger 43 mounted or mountable on a rear end of the gasket 42, and the medical agent 41 filled inside the space formed of the barrel 80, the gasket 42, and the sealing member 90. In this embodiment, the sealing member 90 is formed of the seal cap 90 removable from the barrel.

The prefilled syringe 40 of this embodiment is composed of the barrel 80, the gasket 42, the seal cap 90 serving as the sealing member, and the medical agent 41 filled inside the space formed of the barrel 80, the gasket 42, and the seal cap 90.

The barrel 80 is a tubular body formed of a transparent material or a semitransparent material having preferably a low degree of oxygen and water vapor permeabilities.

The barrel 80 has the barrel body part 81, the distal end part 82 provided at the distal end side of the barrel body part 81, and the flange 84 provided at the rear end side of the barrel body part 81.

The barrel body part 81 is a substantially tubular part accommodating the gasket 42 liquid-tightly and slidably. The nozzle part is formed as a tubular part having a smaller diameter than the barrel body part 81. The distal end side of the barrel body part is formed as a tapered portion whose diameter decreases toward the nozzle part.

Figure 11:
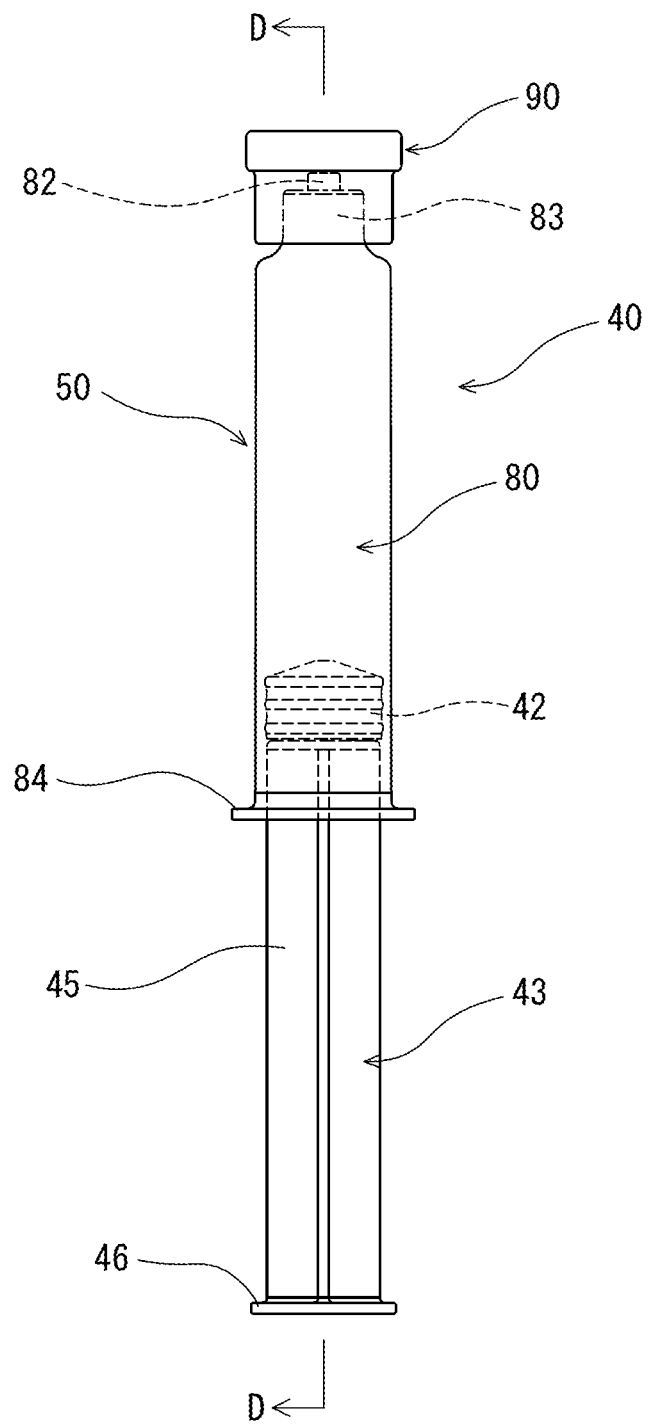
FIG. 11 is a front view of a prefilled syringe of another embodiment of the present invention.
Figure 12:
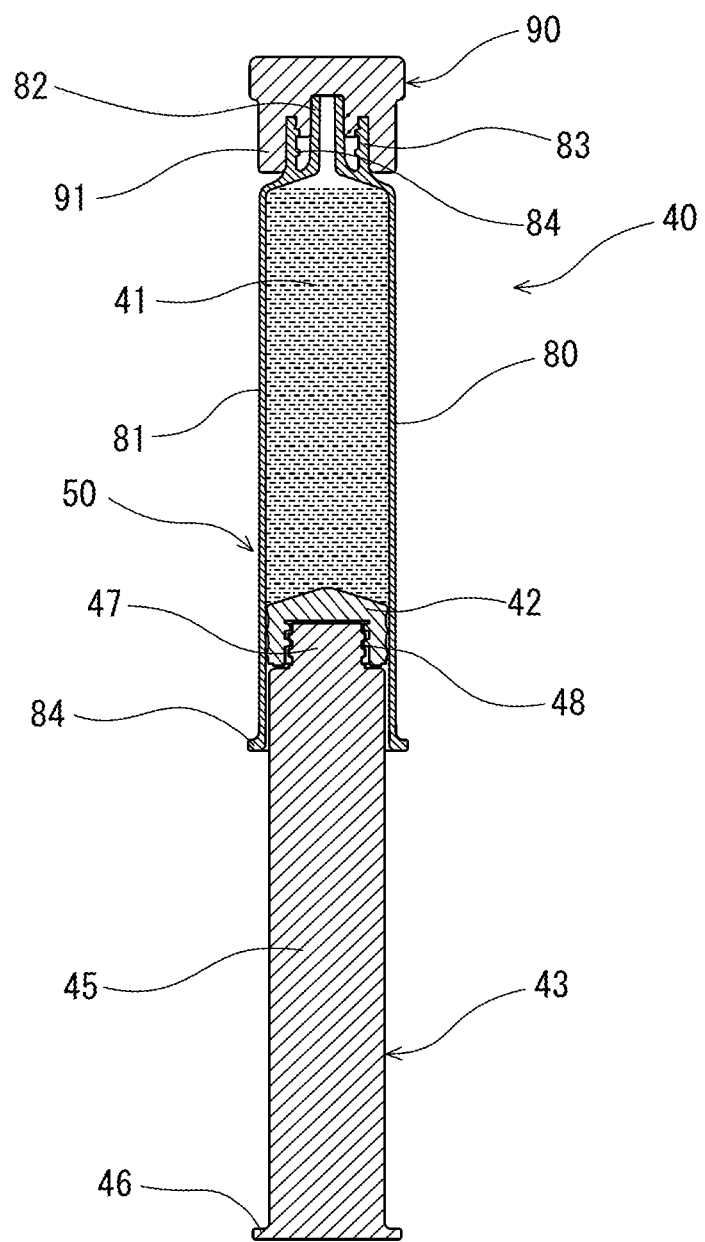
FIG. 12 is a sectional view taken along a line D-D of FIG. 11.
Figure 13:
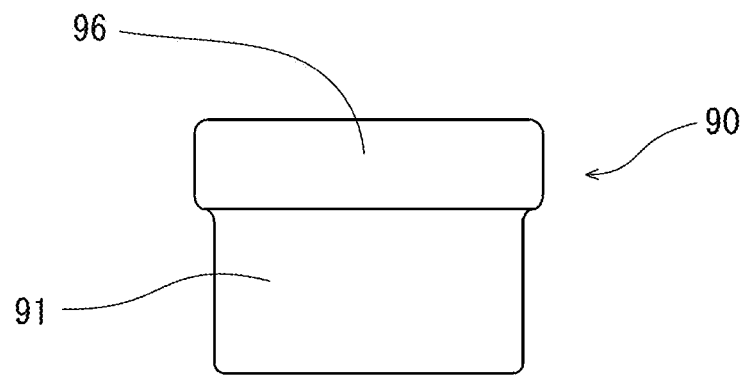
FIG. 13 is an enlarged front view of a seal cap for use in the prefilled syringe shown in FIG. 11.
Figure 14:
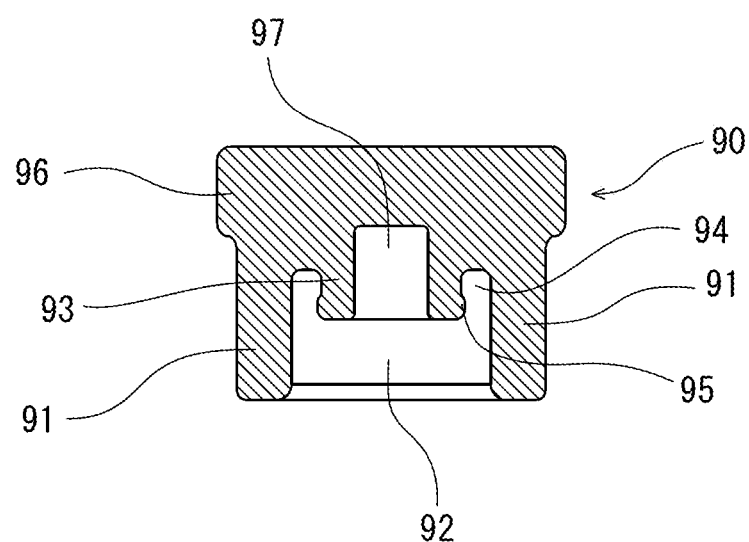
FIG. 14 is a vertical sectional view of the seal cap shown in FIG. 13.

As shown in FIGS. 11 and 12, the flange 84 has an arc-shaped outer edge projected from the entire circumference of the rear end of the barrel body part 81 in a direction vertical to the rear end thereof. In other words, the flange has the shape of a doughnut disk internally deleted.

In this embodiment, as shown in FIG. 12, the barrel 80 has a collar 83 formed concentrically with the distal end part (nozzle part) 82 thereof. The distal end part 82 is provided at the distal part of the barrel 80 and has a distal end opening for discharging a liquid medicine filled inside the barrel. The diameter of the distal end part 82 decreases toward its distal end in a tapered shape. The collar 83 is formed cylindrically and concentrically with the distal end part 82 in such a way as to surround the tubular distal end part 82. The collar 83 is open at its distal end. The inner and outer diameters of the collar 83 are set substantially equally respectively from its proximal end to distal end. The distal end of the distal end part (nozzle part) 82 projects from a distal end opening of the collar 83. The distal end of the distal end part 82 and that of the collar 83 are chamfered to easily accommodate the distal end part 82 and the collar 83 inside the seal cap 90.

On an inner circumferential surface of the collar 83, there is formed a screw groove (barrel side threadedly engaging portion) 84 which engages a rib 95 formed on a short tubular portion 93 of the seal cap 90 described later and a hub (not shown) of an injection needle to be connected to the barrel when the prefilled syringe is used. Thereby the inner circumferential surface of the collar of the barrel 80 and the outer circumferential surface of a nozzle accommodating part of the seal cap 90 engage each other. The screw groove (barrel side threadedly engaging portion) 84 is used as a portion at which the injection needle (hub of injection needle) is mounted after the seal cap 90 is removed from the barrel.

As materials for forming the barrel 80, those described above are used.

As shown in FIGS. 11 through 14, the seal cap 90 has a closed end 96, a tubular body part 91, and a nozzle accommodating part 92 formed inside the tubular body part 91. The nozzle accommodating part 92 has a nozzle tip accommodating portion 97 for accommodating the distal end of the distal end part (nozzle part) 82 of the barrel 80 and an accommodating portion 94 for accommodating the distal end portion of the collar 83. The tubular body part 91 is formed as a cylindrical part closed at its upper end and open at its lower end. The nozzle accommodating part 92 accommodates the distal end part (nozzle part) 82 of the barrel almost entirely. The nozzle accommodating part 92 has the short tubular portion 93 formed downward (toward the open portion) from an inner side of the closed end 96 concentrically with the tubular body part 91. On an outer surface of a lower end portion of the short tubular portion 93, the rib 95 engageable with the threadedly engaging portion 84 formed on the inner surface of the collar 83 is formed.

As materials for forming the seal cap 90, those described above are used.

As shown in FIG. 12, the gasket 42 has a tubular body part extended in a substantially equal outer diameter and a tapered closed part extended from the tubular body part to the distal end of the gasket. A plurality of annular ribs (although three annular ribs are formed in this embodiment, not less than two annular ribs may be formed, provided that the annular rib satisfies liquid tightness and slidability) are formed on the outer surface of the body part. The ribs contact the inner surface of the barrel 80 liquid-tightly.

The gasket 42 has a plunger mounting portion provided inside its tubular body part. In the gasket of this embodiment, the plunger mounting portion is composed of a concave portion and a gasket side threadedly engaging portion 48 formed on an inner surface of the concave portion. The plunger 43 has a gasket mounting part 47 formed at its distal end part. In the plunger of this embodiment, the gasket mounting part 47 is constructed of a projected portion and a plunger side threadedly engaging portion formed on an outer surface of the projected portion.

As materials for forming the gasket 42, it is preferable to use elastic rubber (for example, butyl rubber, Latex rubber, silicone rubber, and the like) and synthetic resin (for example, styrene-based elastomer including SBS elastomer, SEBS elastomer and the like and olefin-based elastomer including ethylene-α olefin copolymer elastomer, and the like).

As shown in FIGS. 11 and 12, the plunger 43 has a plunger body part 45, a gasket mounting part 47 projected from the plunger body part 45 to the distal end of the plunger, and a pressing part 46. The plunger body part 45 has a shaft portion formed in a cross shape in its cross section. The shaft portion is formed of four flat plate portions.

As materials for composing the plunger 43, it is preferable to use rigid resin or semirigid resin such as high-density polyethylene, polypropylene, polystyrene, and polyethylene terephthalate.

As the liquid medicine 41 to be filled inside the space formed of the barrel 80, the gasket 42, and the sealing member, it is possible to exemplify a contrast agent, a high-concentration sodium chloride injection solution, minerals, a heparin sodium injection solution, nitroglycerin, isosorbide dinitrate, cyclosporine, benzodiazepines, antibiotics, vitamin pills (multivitamin pills), various amino acids, an anti-thrombotic agent such as heparin, insulin, an anti-tumor agent, analgesics, a cardiotonic agent, an intravenous anesthetic agent, an anti-Parkinson's agent, a tumor therapeutic agent, an adrenocortical hormone agent, an antiarrhythmic agent, a correction electrolyte, antiviral agent, and an immunostimulant agent. As the liquid medicine 41 to be filled inside the space, it is preferable to use a liquid medicine which is administered to a patient by the prefilled syringe 40 (barrel 80) mounted on an automatic medicine administrating device such as an injector or a syringe pump having a flange accommodating part into which the flange 84 of the barrel 80 has been inserted. As the liquid medicine 41 to be administered to the patient in the above-described manner, a contrast agent for angiography is exemplified.

EXAMPLES

Example 1

Figure 4:
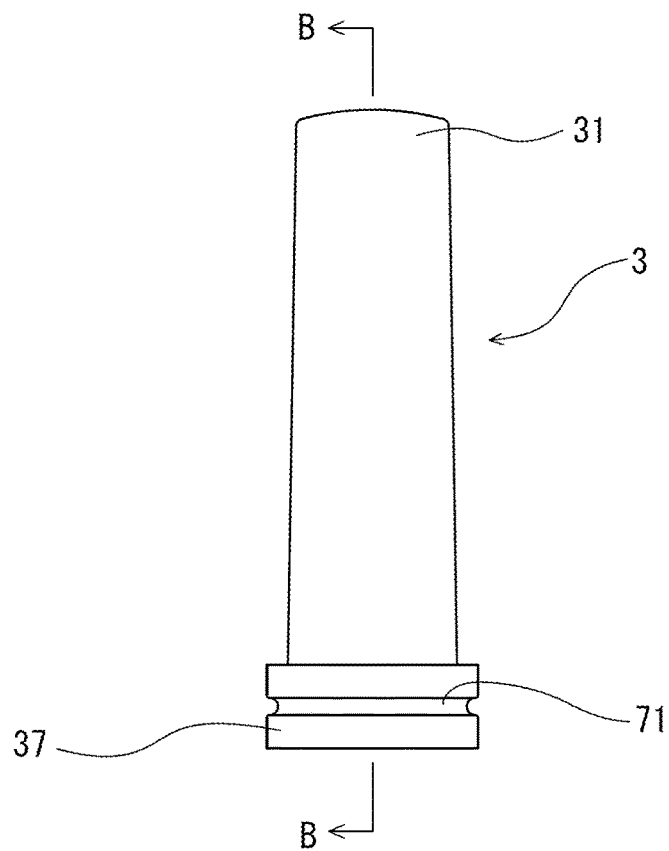
FIG. 4 is an enlarged front view of a seal cap for a barrel for use in the prefilled syringe shown in FIGS. 1 and 2 and the assembly for the syringe shown in FIG. 3.
Figure 5:
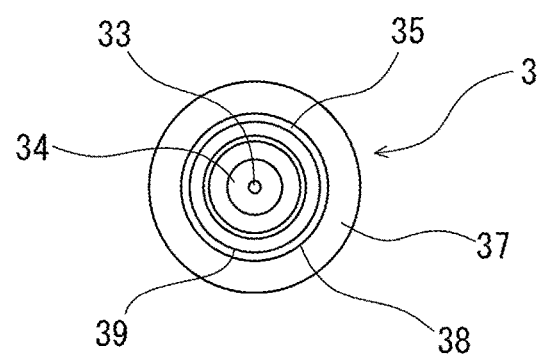
FIG. 5 is a bottom view of the seal cap for the barrel shown in FIG. 4.

The following components were mixed with one another to produce an elastic thermoplastic elastomer composition: 29 parts by weight of a styrene-based thermoplastic elastomer (a hydrogenated styrene-isoprene-butadiene-styrene block copolymer having a weight-average molecular weight of 380,000 and containing 30 percentage by weight of styrene (block P), 12 parts by weight of polypropylene (polypropylene homopolymer having a MFR of 10 g/10 minutes (230 degrees C., 2.16 kg load), 35 parts by weight of a softener for hydrocarbon-based rubber (polybutene having a kinematic viscosity of 590 $mm^2s^{-1}$ at 100 degrees C. and not containing naphthenic carbon), five parts by weight of polyethylene wax having a weight-average molecular weight of 7,100, and 19 parts by weight of talc (average particle diameter of 8.0 μm and specific gravity of 0.25). By using the thermoplastic elastomer, a seal cap having a form as shown in FIGS. 4 through 6 was produced.

In addition, a barrel having a form as shown in FIGS. 7 through 9 was produced. A barrel body was produced by injection molding a cyclic olefin polymer (COP) which is a homopolymer of cyclic olefin.

Example 2

The following components were mixed with one another to produce an elastic thermoplastic elastomer composition: 38 parts by weight of a styrene-based thermoplastic elastomer (a hydrogenated styrene-isoprene-butadiene-styrene block copolymer having a weight-average molecular weight of 380,000 and containing 30 percentage by weight of styrene (block P), nine parts by weight of polypropylene (polypropylene homopolymer having a MFR of 10 g/10 minutes (230 degrees C., 2.16 kg load), 48 parts by weight of a softener for hydrocarbon-based rubber (ethylene-propylene copolymer having a kinematic viscosity of 40 $mm^2s^{-1}$ at 100 degrees C. and zero in the content ratio of naphthenic carbon), and five parts by weight of polyethylene wax having a weight-average molecular weight of 7,100. A seal cap was produced in a manner similar to that of the example 1 except that the produced elastic thermoplastic elastomer composition was used as the material of the seal cap. The same barrel as that of the example 1 was used.

Comparison Example 1

The following components were mixed with one another to produce an elastic thermoplastic elastomer composition: 40 parts by weight of a styrene-based thermoplastic elastomer (a hydrogenated styrene-isoprene-butadiene-styrene block copolymer having a weight-average molecular weight of 380,000 and containing 30 percentage by weight of styrene (block P), 10 parts by weight of polypropylene (polypropylene homopolymer having a MFR of 10 g/10 minutes (230 degrees C., 2.16 kg load), and 50 parts by weight of a softener for hydrocarbon-based rubber (paraffinic process having naphthenic carbon ratio of 28%) were mixed with one another. A seal cap was produced in a manner similar to that of the example 1 except that the above-described elastic thermoplastic elastomer composition was used as the material for forming the seal cap. The same barrel as that of the example 1 was used.

Comparison Example 2

A product was formed on the inner surface of the seal cap of the comparison example 1 by polymerizing (including crosslinking) a liquid coating agent (trade name: MDX4-4159 produced by Dow Corning Toray Co., Ltd.) containing reactive silicone oil as its main component at normal temperature or by heating the liquid coating agent. Except that the seal cap of the comparison example 1 was used, an operation similar to that of the example 1 was carried out.

Experiment 1: Removal Strength Test

After silicone was applied to the needle tip of a piercing needle, seal caps of the examples 1, 2 and the comparison examples 1, 2 were mounted on barrels respectively at a predetermined position thereof. An internal pressure inside the seal cap rises when the seal cap is mounted on the barrel. Thus, a gap was formed between the barrel and the seal cap by deforming a portion of the seal cap in the vicinity of the open portion thereof so as to release the internal pressure. After the seal cap was mounted on the barrel, the seal cap and the barrel were subjected to autoclave treatment (123 degrees C., 85 minutes). After a hook was put on the distal end of the seal cap, a flange of the barrel was fixed to conduct a tensile test by using an autograph (load cell MAX100N). In this manner, the removal strength of the seal cap was measured. The test results were as shown in table 1.

It is favorable that the seal cap has a low removal strength and more favorable that the seal cap has a removal strength not more than 25N. The mark of "○" in the removal strength column of table 1 indicates that the removal strength of the seal cap was not more than 25N and that the mark of "x" indicates that the removal strength thereof exceeded 25N. It could be confirmed that the seal caps of the examples 1, 2 had a lower removal strength and a more excellent sticking restraining effect than the seal caps of the comparison examples 1, 2.

Experiment 2: Measurement of Water Vapor Permeability

The thermoplastic elastomer for forming the seal cap of each of the examples 1, 2 and the comparison examples 1, 2 prepared in the above-described manner was press molded at 200 degrees C. by a press molding machine to prepare press sheets each having a thickness of 0.5 mm. The water vapor permeability of each sheet was measured. In measuring the water vapor permeability, a water vapor test was conducted at 40 degrees C. in accordance with "Plastics Film and sheeting: Determination of water vapour transmission rate Instrumental method" described in JIS K7129 (revised on 2008 Mar. 20). The test results were as shown in table 1. In the experiment, it could be confirmed that the material for forming the seal caps of the examples 1, 2 and the comparison examples 1, 2 had satisfactory water vapor permeability.

Apparatus: PERMATRAN-W 3/31
Temperature and humidity: 40 degrees C., 90% RH
Permeation area: 50 cm$^2$ Experiment 3: Sterility Test The seal cap of each of the examples 1, 2 and the comparison examples 1, 2 produced in the above-described manner and needle-attached barrels were prepared by individually sterilizing them. After BI bacteria (2.7×10$^6$CFU/ml) was filled in each seal cap, five syringe assemblies in each of which the seal cap was mounted on the barrel were prepared. Because the internal pressure inside the seal cap rises when the seal cap is mounted on the barrel, the neighborhood of the open portion of the seal cap was deformed to form a gap between the barrel and the seal cap so that the internal pressure of the seal cap was released. After the seal cap was mounted on the barrel, the syringe assemblies were subjected to autoclave treatment (123 degrees C., 20 minutes). After the syringe assemblies were sterilized, culture medium treatment was performed for seven days. The results were as shown in table 1. In the sterility column of table 1, the mark of "○" shows that the BI bacteria could be sterilized (all bacteria were killed) and the mark of "x" shows that the BI bacteria could not be sterilized (none of bacteria was killed). It could be confirmed that the seal caps of the examples 1, 2 and the comparison examples 1, 2 had autoclave sterilization performance.

Experiment 4: Ozone Resistance Test

In accordance with "Rubber, vulcanized or thermoplastic-Determination of ozone resistance" described in JIS K 6249 (revised on 2004 Mar. 20), a test was conducted on 10 sterilized syringe assemblies of each of the examples 1, 2 and the comparison examples 1, 2 produced in the above-described manner. After the syringe assemblies were exposed to an ozone environment, the seal caps were checked whether they were resistant to ozone. The results were as shown in table 1. The mark of "○" in table 1 shows that the seal cap was resistant to ozone (ozone-caused deterioration in its appearance was not recognized). The mark of "x" shows that the seal cap was not resistant to ozone (ozone-caused deterioration in its appearance was recognized). It could be confirmed that the seal caps of the examples 1, 2 and comparison examples 1, 2 were resistant to ozone.

Experiment 5: Piercing Resistance Test

A piercing resistance test was conducted on 20 sterilized syringe assemblies of each of the examples 1, 2 and the comparison examples 1, 2 produced in the above-described manner. After the seal cap was removed from the barrel, the piercing resistance of each needle to silicone rubber (t=0.5 mm) was measured by using an autograph. The results were as shown in table 1. It is favorable that the needle has a low piercing resistance and more favorable that the needle tip has a piercing resistance of not more than 0.2. The mark of "○" in the piercing resistance column of table 1 indicates that the piercing resistance of the needle tip was not more than 0.2N.

It could be confirmed that the needle tips pierced into the seal caps of the examples 1, 2 and the comparison examples 1, 2 had a sufficiently high piercing property.

TABLE 1

|  | Removal strength | Water vapor permeability | Sterility | Ozone resistance | Piercing resistance |
|---|---|---|---|---|---|
| Example 1 | ○ 23N | 1.4 g/(m$^2$ · 24 h) | ○ | ○ | ○ 0.13N |
| Example 2 | ○ 11N | 5.3 g/(m$^2$ · 24 h) | ○ | ○ | ○ 0.14N |
| Comparison example 1 | x 31N | 4.5 g/(m$^2$ · 24 h) | ○ | ○ | ○ 0.14N |
| Comparison example 2 | x31N 30N | 4.5 g/(m$^2$ · 24 h) | ○ | ○ | ○ 0.13N |

Embodiments of a package, shown in the drawings, which accommodates a plurality of the assemblies of the present invention for syringes are described below by using FIGS. 15 through 19.

A package 100 of the present invention for the assembly for the prefilled syringe, accommodating a plurality of assemblies for syringes, which can be or is subjected to sterilization has a container body 102 whose upper surface is open and which has shape retainability, a barrel holding member 104 capable of holding a plurality of assemblies 10 for syringes accommodated inside the container body 102, a plurality of the assemblies 10 for syringes held by the barrel holding member 104, and a sheet-shaped lid member 103 which air tightly seals the open upper surface of the container body 102 and is peelable from the container body.

The package 100 of the present invention for the assembly for the prefilled syringe can be or is subjected to sterilization. As a sterilization method, the high-pressure steam sterilization, radiation or electron beam sterilization, and the ethylene oxide gas sterilization are used.

Figure 15:
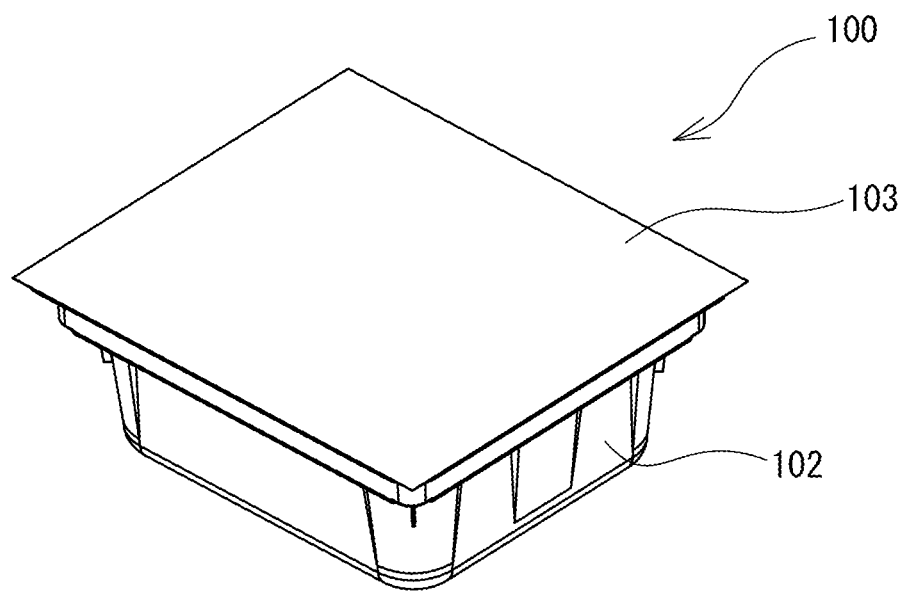
FIG. 15 is a perspective view of a package of the present invention for an assembly for a syringe.
Figure 16:
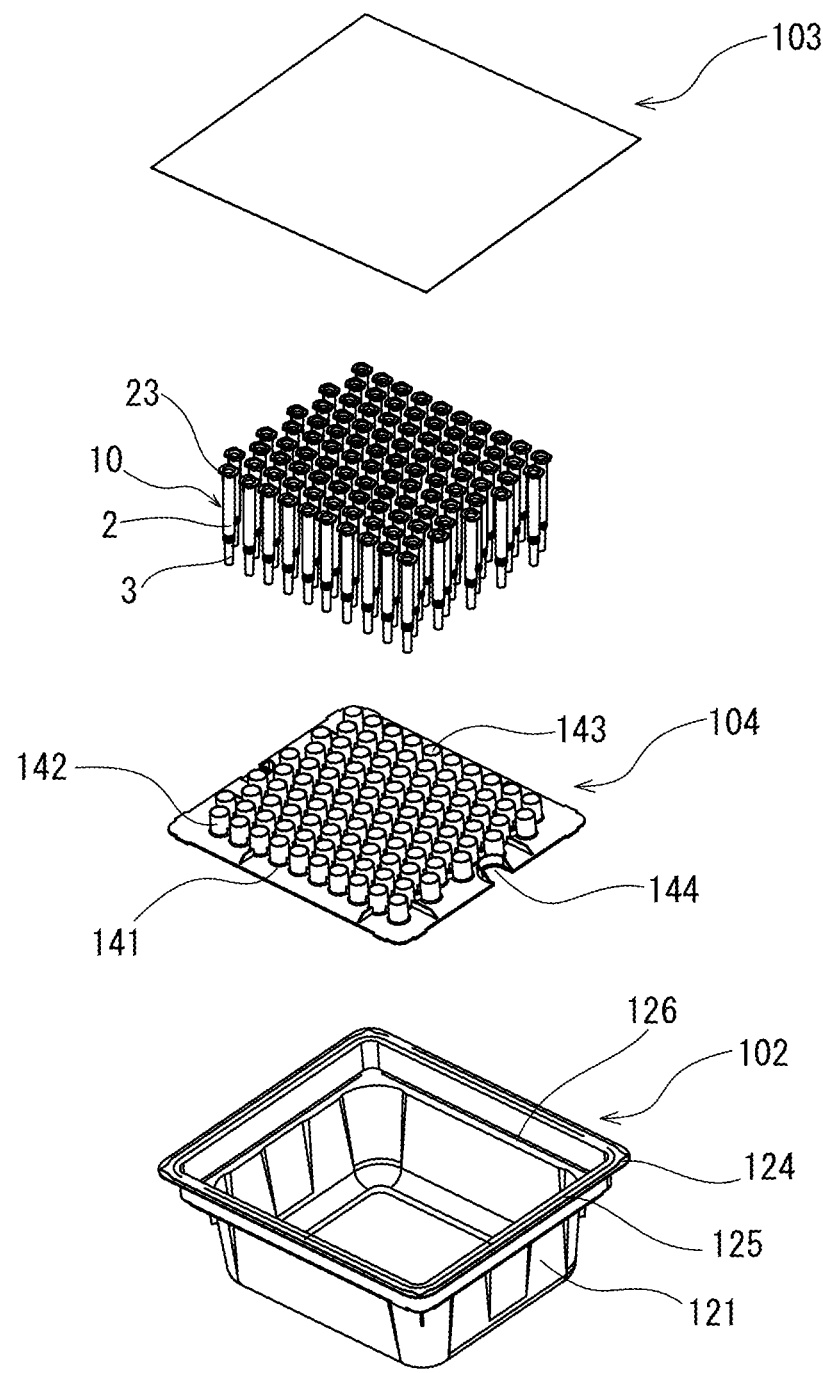
FIG. 16 an explanatory view for explaining an inner form of the package for the assembly for the syringe shown in FIG. 15.
Figure 17:
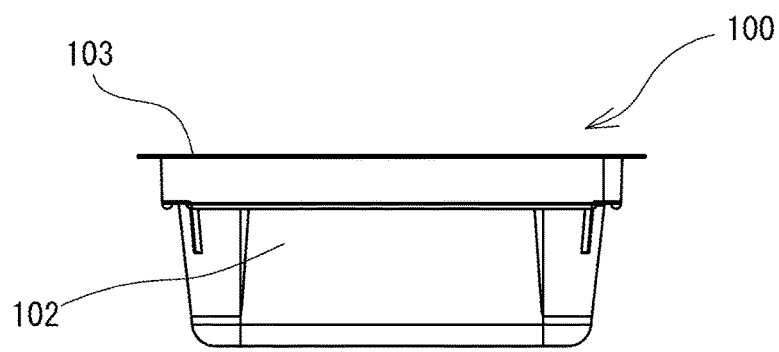
FIG. 17 is a front view of the package for the assembly for the syringe shown in FIG. 15.
Figure 18:
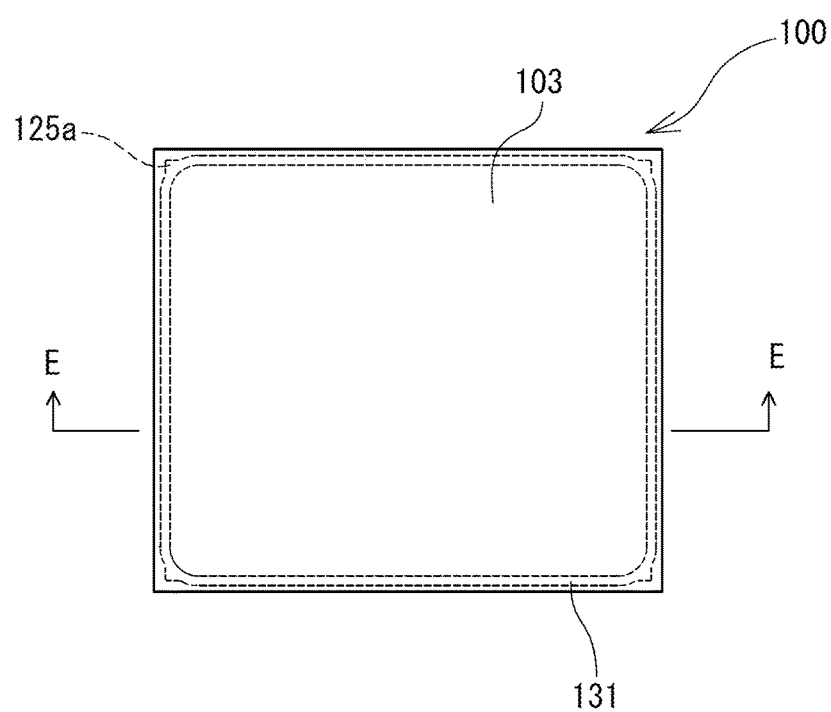
FIG. 18 is a plan view of the package for the assembly for the syringe shown in FIG. 17.

As shown in FIGS. 15, 16, and 19, the package 100 of the present invention for the assembly for the prefilled syringe has the container body 102, the barrel holding member 104 capable of holding a plurality of assemblies 10 for syringes, a plurality of the assemblies 10 for syringes held by the barrel holding member 104, and the sheet-shaped lid member 103 which air tightly seals the open upper surface of the container body 102 and is peelable therefrom. The package further includes an air-permeable part, having bacteria impermeability and sterilizing gas permeability, which is provided on the container body 102 or on the sheet-shaped lid member 103.

As shown in FIGS. 15 through 19, the container body 102 is tray-shaped and has a strength and shape retainability to some extent and a predetermined depth. The container body 102 has a body part 121, a barrel holding member-holding portion 126, formed at an upper portion of the body part 121, for holding a peripheral portion of the barrel holding member 104 which holds a plurality of the assemblies 10 for syringes, and an annular flange 124 formed at the opening of the upper surface of the container body.

An annular heat-sealing convex portion 125 is formed on the upper surface of the annular flange 124 to fix the sheet-shaped lid member 103 to the heat-sealing convex portion 125. The barrel holding member-holding portion 126 is formed at a position located below the flange 124 by spacing it at a predetermined interval from the flange 124. In the container body 102 of a first embodiment, the barrel holding member-holding portion 126 is formed as an annular stepped portion so that the peripheral portion of the barrel holding member 104 which holds a plurality of the assemblies 10 for syringes can be placed thereon.

It is preferable that the container body 102 has shape retainability and rigidity to some extent. To respond to the high-pressure steam sterilization, it is desirable to use a thermoplastic material having heat resistance (not less than 120 degrees C.). As materials having the shape retainability and the rigidity to some extent, heat resistance, and thermoplasticity, it is possible to exemplify polyolefin such as polypropylene and polyethylene, vinyl chloride resin, polystyrene/polypropylene resin, polyethylene/ionomer (for example, ethylene-based, styrene-based, fluorine-based)/polyethylene, polyester resin (for example, polyethylene terephthalate, polybutylene terephthalate, and amorphous polyethylene terephthalate), and PP/EVOH/PP (laminate) are listed. In this case, the thickness of the container 102 is set to favorably 0.05 to 4.00 mm and especially favorably 1.00 to 2.00 mm.

It is possible to subject the container body 102 to radiation sterilization or electron beam sterilization. In this case, it is desirable to use radiation-resistant material. As the radiation-resistant material (for example, radiation-resistant polyolefin), it is possible to use polyolefin (for example, polypropylene, polyethylene) to which hindered amine, an antioxidant, a nucleating agent, and the like are added to impart radiation resistance thereto. As the hindered amine, bis(2,2,6,6-tetramethylpiperidyl)sebacate, bis(2,2,6,6-tetramethylpiperidyl)adipate, bis(2,2,6,6-tetramethylpiperidyl)fumarate are exemplified. As the antioxidant, 1,1,3-tris (2-methyl-hydroxy-5-t-butylphenyl)butane, tris(3,5-di-T-butyl-4-hydroxybenzyl) isocyanurate, tetrakis(methylene-3-(3,5-di-t-butyl-4-hydroxyphenyl) propionate)methane. As the nucleating agent, 1,3,2,4-dibenzylidene sorbitol and 1,3,2,4-di(p-methylbenzylidene) sorbitol are exemplified.

As shown in FIGS. 16 and 19, the barrel holding member 104 capable of holding a plurality of the assemblies 10 for syringes has a substrate part 141 and a plurality of cylindrical parts 142 projecting upward from the substrate part 141. A barrel holding open portion 143 is formed inside each tubular part 142. A gripping cut-out 144 is formed on sides of the substrate part 141. The inner diameter of the tubular part 142 and that of the barrel holding open portion 143 are set larger than the outer diameter of a maximum diameter portion of the assembly 10 for the syringe held by the barrel holding member. It is impossible for the flange 23 of the assembly 10 for the syringe held by the barrel holding member to pass through the tubular part 142 and the barrel holding open portion 143.

Therefore, as shown in FIG. 19, the assembly 10 for the syringe passes through the cylindrical part 142, and the flange 23 of the assembly 10 for the syringe is hung by the barrel holding open portion 143. As shown in FIG. 19, the lower end (the distal end of the seal cap 3) of the assembly 10 for the syringe held by the barrel holding member 104 does not contact the bottom surface of the container body 102. In other words, the bottom surface of the container body 102 and the lower end (distal end of the seal cap 3) of the assembly 10 for the syringe held by the barrel holding member 104 are spaced away from each other so that the space therebetween does not inhibit the circulation of water vapor. It is desirable that a material for forming the barrel holding member 104 has heat resistance (not less than 120 degrees C.) so that the barrel holding member is capable of responding to the high-pressure steam sterilization.

It is desirable that the sheet-shaped lid member 103 has a property of not allowing fine particles such as bacteria and virus to permeate therethrough to perform the high-pressure steam sterilization or the ethylene oxide gas sterilization and has a sterilizing gas-permeable property of allowing a sterilizing gas such as water vapor and ethylene oxide gas to permeate therethrough. It is preferable that the sheet-shaped lid member 103 can be heat-sealed to the container body 102. For example, it is possible to suitably use nonwoven cloth made of synthetic resin for the sheet-shaped lid member. More specifically, it is possible to use nonwoven cloth, known as Tyvek (registered trademark), which is made of a synthetic resin material such as polyolefin and a porous film made of synthetic resin for the sheet-shaped lid member.

The peripheral portion of the sheet-shaped lid member 103 is peelably heat-sealed to the heat-sealing convex portion 125 formed on the annular flange 124 of the container body 102. In the first embodiment, the outer edge of the sheet-shaped lid member 103 is not heat-sealed to the annular flange 124 of the container body 102 to easily peel the sheet-shaped lid member from the container body. A projected portion 125a formed at each corner of the heat-sealing convex portion 125 functions as a peeling starting portion. The thickness of the sheet-shaped lid member 103 is set to favorably 0.05 to 1.00 mm and more favorably 0.10 to 0.50 mm.

In the first embodiment, the air-permeable part is provided on the sheet-shaped lid member 103. The air-permeable part-forming position is not limited to the sheet-shaped lid member, but may be formed on the container body 102.

In a case where the package 100 for the assembly for the prefilled syringe is stored with the seal cap 3 being mounted on the barrel 2 and in a case where the package 100 for the assembly for the prefilled syringe undergoes the high-pressure steam sterilization or the ethylene oxide gas sterilization which subjects the assembly for the syringe to a pressure load, it is possible to restrain the inner surface of the piercing needle fixing portion accommodating part 35 and the outer surface of the piercing needle fixing portion 22 from sticking to each other.

INDUSTRIAL APPLICABILITY

The assembly of the present invention for the syringe has the following form:

(1) An assembly for a syringe comprising a barrel having a barrel body having a distal end part and a seal cap mounted on said distal end part of said barrel, wherein said seal cap is formed of a thermoplastic elastomer composition containing as a main component thereof a mixture of a styrene-based thermoplastic elastomer and a softener for hydrocarbon-based rubber, said softener for hydrocarbon-based rubber has a kinematic viscosity of 1 to 5,000 $mm^2s^{-1}$ at 100 degrees C. and a naphthenic carbon ratio (% CN) of not more than 20% when said naphthenic carbon ratio is measured by ring analysis; and said barrel body of said barrel is formed of cyclic polyolefin.

In the assembly of the present invention for the syringe, the seal cap is formed of the thermoplastic elastomer composition containing the mixture of the styrene-based thermoplastic elastomer and the softener for hydrocarbon-based rubber as its main component. Therefore, the seal cap is highly elastic. Further the softener for the hydrocarbon-based rubber is highly compatible with the thermoplastic resin. In addition, the thermoplastic elastomer composition containing the softener for the hydrocarbon-based rubber has a low degree of permeability into the cyclic polyolefin. Thus, in a case where the assembly for the syringe undergoes high-pressure steam sterilization which subjects the assembly for the syringe to a pressure load and in a case where the assembly for the syringe is stored with the seal cap being mounted on the barrel, the inner surface of the seal cap and the outer surface of the distal end part of the barrel made of the cyclic polyolefin do not stick to each other. Consequently, it does not occur that the cap is removed from the barrel. In addition, in the assembly for the syringe, the seal cap has a satisfactory autoclave sterilization performance. Further, even though the seal cap contacts ozone when it is produced or stored, the seal cap does not deteriorate or crack owing to the contact between it and ozone.

The above-described embodiment may be carried out as follows:

(2) An assembly for a syringe according to the above (1), which can be or is subjected to high-pressure steam sterilization.

(3) An assembly for a syringe according to the above (1) or (2), wherein said thermoplastic elastomer composition contains 20 to 70 percentage by weight of said softener for said hydrocarbon-based rubber.

(4) An assembly for a syringe according to any one of the above (1) through (3), wherein said styrene-based thermoplastic elastomer consists of a block copolymer having at least one polymer block P containing a vinyl aromatic compound as a main component thereof and at least one polymer block Q containing conjugated diene and/or isobutylene as a main component thereof and/or a hydrogenated block copolymer to be obtained by hydrogenating said block copolymer.

(5) An assembly for a syringe according to any one of the above (1) through (4), wherein said seal cap has a closed distal end part, an open proximal end part, a hollow part extended from said open proximal end part toward a distal end of said seal cap; said hollow part has a distal end part accommodating portion for accommodating said distal end part of said barrel; and said distal end part accommodating portion of said seal cap accommodates said distal end part of said barrel body with said distal end part accommodating portion of said seal cap in close contact with said distal end part of said barrel body.

(6) An assembly for a syringe according to any one of the above (1) through (5), wherein said barrel has a piercing needle fixing portion provided at said distal end part of said barrel body and a piercing needle which has a piercing needle tip at a distal end thereof and whose proximal end portion is fixed to said piercing needle fixing portion.

(7) An assembly for a syringe according to the above (6), wherein said distal end part accommodating portion accommodates said piercing needle fixing portion of said barrel.

(8) An assembly for a syringe according to the above (6) or (7), wherein said seal cap has a pierceable part into which said piercing needle tip of said piercing needle inserted into said hollow part can be pierced, so that said assembly has a state in which said piercing needle is pierced into said pierceable part.

(9) A prefilled syringe according to any one of the above (1) through (5), wherein said distal end part of said barrel is an open portion and said open portion is sealed by said seal cap.

The prefilled syringe of the present invention has the following form:

(10) A prefilled syringe comprising an assembly for a syringe according to any one of the above (1) through (9), a gasket which is accommodated inside said barrel and liquid-tightly slidable inside said barrel, and a medical agent filled inside a space formed of said barrel and said gasket.

Therefore, in a case where the seal cap is stored for a predetermined period of time with the seal cap being mounted on the barrel made of the cyclic polyolefin, the seal cap does not stick to the barrel and thus, can be easily removed therefrom.

The seal cap of the present invention for the barrel has the following form:

(11) A seal cap for a barrel to be mounted on a distal end part of a barrel for a syringe, wherein said seal cap is formed of a thermoplastic elastomer composition containing as a main component thereof a mixture of a styrene-based thermoplastic elastomer and a softener for hydrocarbon-based rubber, said softener for hydrocarbon-based rubber has a kinematic viscosity of 1 to 5,000 $mm^2s^{-1}$ at 100 degrees C. and a naphthenic carbon ratio (% CN) of not more than 20% when said naphthenic carbon ratio is measured by ring analysis.

Because the seal cap of the present invention for the barrel is formed of the thermoplastic elastomer composition containing the softener for hydrocarbon-based rubber, the seal cap is highly elastic. Further in a case where the seal cap is stored for a predetermined period of time with the seal cap being mounted on the barrel made of the cyclic polyolefin, the seal cap does not stick to the barrel. Because the seal cap has water vapor permeability, it has satisfactory autoclave sterilization performance. Further, even though the seal cap contacts ozone when it is produced or stored, the seal cap does not deteriorate or crack owing to the contact between it and ozone.

The above-described embodiments may be carried out as described below.

(12) A seal cap for a barrel according to the above (11), said seal cap being used for a barrel made of cyclic polyolefin.

(13) A seal cap for a barrel according to the above (11) or (12), wherein said thermoplastic elastomer composition contains 20 to 70 percentage by weight of said softener for said hydrocarbon-based rubber.

(14) A seal cap for a barrel according to any one of the above (11) through (13), wherein said styrene-based thermoplastic elastomer consists of a block copolymer having at least one polymer block P containing a vinyl aromatic compound as a main component thereof and at least one polymer block Q containing conjugated diene and/or isobutylene as a main component thereof and/or a hydrogenated block copolymer to be obtained by hydrogenating said block copolymer.

(15) A seal cap for a barrel according to any one of the above (11) through (14), wherein said seal cap has a closed distal end part, an open proximal end part, a hollow part extended from said open proximal end part toward a distal end of said seal cap; and said hollow part has a distal end part accommodating portion for accommodating said distal end part of said barrel.

(16) A seal cap for a barrel according to any one of the above (11) through (14), wherein said distal end part of said barrel is an open portion and said open portion is sealed by said seal cap.

The package of the present invention for the assembly for the syringe has the following form:

(17) A package, for an assembly for a syringe, for accommodating a plurality of assemblies for syringes according to any one of the above (1) through (9), said package comprising a container body whose upper surface is open and which has shape retainability, a barrel holding member capable of holding a plurality of said assemblies for syringes, a plurality of said assemblies for syringes held by said barrel holding member, and a sheet-shaped lid member which air tightly seals said open upper surface of said container body and is peelable therefrom, and an air-permeable part, having bacteria impermeability and sterilizing gas permeability, which is provided on said container body or on said sheet-shaped lid member, and said package accommodated a plurality of said assemblies for syringes was subjected to high-pressure steam sterilization.

The invention claimed is:

1. An assembly for a syringe comprising a barrel having a barrel body having a distal end part and a seal cap mounted on said distal end part of said barrel,
    wherein said seal cap is formed of a thermoplastic elastomer composition containing as a main component thereof a mixture of a styrene-based thermoplastic elastomer and a softener for hydrocarbon-based rubber,
    said softener for hydrocarbon-based rubber has a kinematic viscosity of 1 to 5,000 $mm^2s^{-1}$ at 100 degrees C. and a naphthenic carbon ratio (% CN) of not more than 20% when said naphthenic carbon ratio is measured by ring analysis; and said barrel body of said barrel is formed of cyclic polyolefin.

2. An assembly for a syringe according to claim 1, which can be or is subjected to high-pressure steam sterilization.

3. An assembly for a syringe according to claim 1, wherein said thermoplastic elastomer composition contains 20 to 70 percentage by weight of said softener for said hydrocarbon-based rubber.

4. An assembly for a syringe according to claim 1, wherein said styrene-based thermoplastic elastomer consists of a block copolymer having at least one polymer block P containing a vinyl aromatic compound as a main component thereof and at least one polymer block Q containing conjugated diene and/or isobutylene as a main component thereof and/or a hydrogenated block copolymer to be obtained by hydrogenating said block copolymer.

5. An assembly for a syringe according to claim 1, wherein said seal cap has a closed distal end part, an open proximal end part, a hollow part extended from said open proximal end part toward a distal end of said seal cap; said hollow part has a distal end part accommodating portion for accommodating said distal end part of said barrel; and said distal end part accommodating portion of said seal cap accommodates said distal end part of said barrel body with said distal end part accommodating portion of said seal cap in close contact with said distal end part of said barrel body.

6. An assembly for a syringe according to claim 1, wherein said distal end part of said barrel is an open portion and said open portion is sealed by said seal cap.

7. An assembly for a syringe according to claim 1, wherein said softener for said hydrocarbon-based rubber has an aromatic carbon ratio (% CA) of not more than 5% when the aromatic carbon ratio is measured by ring analysis.

8. An assembly for a syringe according to claim 1, wherein said barrel has a piercing needle fixing portion provided at said distal end part of said barrel body and a piercing needle which has a piercing needle tip at a distal end thereof and whose proximal end portion is fixed to said piercing needle fixing portion.

9. An assembly for a syringe according to claim 8, wherein said distal end part accommodating portion accommodates said piercing needle fixing portion of said barrel.

10. An assembly for a syringe according to claim 8, wherein said seal cap has a pierceable part into which said piercing needle tip of said piercing needle inserted into said hollow part can be pierced, so that said assembly has a state in which said piercing needle tip is pierced into said pierceable part of said seal cap.

11. A prefilled syringe comprising an assembly for a syringe according to claim 1, a gasket which is accommodated inside said barrel and liquid-tightly slidable inside said barrel, and a medical agent filled inside a space formed of said barrel and said gasket.

12. A seal cap for a barrel to be mounted on a distal end part of a barrel for a syringe,
    wherein said seal cap is formed of a thermoplastic elastomer composition containing as a main component thereof a mixture of a styrene-based thermoplastic elastomer and a softener for hydrocarbon-based rubber,
    said softener for hydrocarbon-based rubber has a kinematic viscosity of 1 to 5,000 $mm^2s^{-1}$ at 100 degrees C. and a naphthenic carbon ratio (% CN) of not more than 20% when said naphthenic carbon ratio is measured by ring analysis.

13. A seal cap for a barrel according to claim 12, said seal cap being used for a barrel made of cyclic polyolefin.

14. A seal cap for a barrel according to claim 12, wherein said thermoplastic elastomer composition contains 20 to 70 percentage by weight of said softener for said hydrocarbon-based rubber.

15. A seal cap for a barrel according to claim 12, wherein said styrene-based thermoplastic elastomer consists of a block copolymer having at least one polymer block P containing a vinyl aromatic compound as a main component thereof and at least one polymer block Q containing conjugated diene and/or isobutylene as a main component thereof and/or a hydrogenated block copolymer to be obtained by hydrogenating said block copolymer.

16. A seal cap for a barrel according to claim 12, wherein said seal cap has a closed distal end part, an open proximal end part, a hollow part extended from said open proximal end part toward a distal end of said seal cap; and said hollow part has a distal end part accommodating portion for accommodating said distal end part of said barrel.

17. A seal cap for a barrel according to claim 12, wherein said distal end part of said barrel is an open portion and said open portion is sealed by said seal cap.

18. A package, for an assembly for a syringe, for accommodating a plurality of assemblies for syringes according to claim 1,
    said package comprising a container body whose upper surface is open and which has shape retainability, a barrel holding member capable of holding a plurality of said assemblies for syringes, a plurality of said assemblies for syringes held by said barrel holding member, and a sheet-shaped lid member which airtightly seals said open upper surface of said container body and is peelable therefrom, and an air-permeable part, having bacteria impermeability and sterilizing gas permeability, which is provided on said container body or on said sheet-shaped lid member, and said package accommodated a plurality of said assemblies for syringes was subjected to high-pressure steam sterilization.

* * * * *